(12) United States Patent
Itsuji et al.

(10) Patent No.: US 8,129,683 B2
(45) Date of Patent: Mar. 6, 2012

(54) WAVEFORM INFORMATION ACQUISITION APPARATUS AND WAVEFORM INFORMATION ACQUISITION METHOD

(75) Inventors: Takeaki Itsuji, Hiratsuka (JP); Shintaro Kasai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 106 days.

(21) Appl. No.: 12/680,889

(22) PCT Filed: Dec. 25, 2008

(86) PCT No.: PCT/JP2008/073925
§ 371 (c)(1),
(2), (4) Date: Mar. 30, 2010

(87) PCT Pub. No.: WO2009/084712
PCT Pub. Date: Jul. 9, 2009

(65) Prior Publication Data
US 2010/0258727 A1    Oct. 14, 2010

(30) Foreign Application Priority Data

Dec. 28, 2007 (JP) ................... 2007-340392
Nov. 10, 2008 (JP) ................... 2008-287755

(51) Int. Cl.
*G01J 5/02* (2006.01)
(52) U.S. Cl. .................................. 250/341.1
(58) Field of Classification Search ........... 250/338.4, 250/339.06, 339.07, 340, 341.1, 343, 347, 250/351, 503.1
See application file for complete search history.

(56) References Cited

U.S. PATENT DOCUMENTS 5,032,975 A    7/1991  Yamamoto et al.
6,448,553 B1    9/2002  Itsuji et al.
(Continued)

FOREIGN PATENT DOCUMENTS

DE    10 2006 04264    3/2008
(Continued)

OTHER PUBLICATIONS

H. Heiliger, et al., "Low-dispersion thin-film microstrip lines with cyclotene (benzocyclobutene) as dielectric medium", Appl. Phys. Lett. 70, vol. 17, pp. 2233-2235, American Institute of Physics, (1997).

(Continued)

*Primary Examiner* — David Porta
*Assistant Examiner* — Marcus Taningco
(74) *Attorney, Agent, or Firm* — Fitzpatrick, Cella, Harper & Scinto

(57) ABSTRACT

Provided are an apparatus and a method which enable acquisition of a temporal waveform of a propagating terahertz wave by changing a propagation velocity of the terahertz wave. A waveform information acquisition apparatus includes a generation portion for generating a terahertz wave, a propagation portion for allowing the terahertz wave generated by the generation portion to propagate therethrough, a detection portion for detecting waveform information of the terahertz wave, a first delay portion for changing a propagation velocity of the terahertz wave, and a control portion for controlling the first delay portion to change the propagation velocity of the terahertz wave in the propagation portion, and acquires information regarding the temporal waveform of the terahertz wave detected by the detection portion.

14 Claims, 13 Drawing Sheets

U.S. PATENT DOCUMENTS

| | | | |
|---|---|---|---|
| 6,828,558 B1 * | 12/2004 | Arnone et al. | 250/341.1 |
| 6,835,925 B2 | 12/2004 | Itsuji et al. | |
| 7,016,102 B2 * | 3/2006 | Trutna et al. | 359/327 |
| 7,248,995 B2 | 7/2007 | Itsuji et al. | |
| 7,358,918 B2 | 4/2008 | Itsuji | |
| 7,542,000 B2 | 6/2009 | Itsuji | |
| 7,557,588 B2 | 7/2009 | Ouchi et al. | |
| 7,560,695 B2 | 7/2009 | Kasai et al. | |
| 7,570,216 B2 | 8/2009 | Itsuji | |
| 7,633,299 B2 | 12/2009 | Itsuji | |
| 2006/0085160 A1 | 4/2006 | Ouchi | 702/150 |
| 2007/0030115 A1 | 2/2007 | Itsuji et al. | |
| 2007/0164842 A1 * | 7/2007 | Koenig | 333/219.2 |
| 2007/0229094 A1 | 10/2007 | Kasai et al. | |
| 2008/0210873 A1 | 9/2008 | Itsuji | 250/347 |
| 2008/0315098 A1 | 12/2008 | Itsuji | |
| 2009/0146084 A1 | 6/2009 | Itsuji | |
| 2009/0189078 A1 | 7/2009 | Itsuji | |
| 2009/0201030 A1 | 8/2009 | Ouchi et al. | |
| 2009/0236529 A1 | 9/2009 | Kasai et al. | |
| 2009/0267858 A1 | 10/2009 | Itsuji | |
| 2010/0052083 A1 | 3/2010 | Kasai | |

FOREIGN PATENT DOCUMENTS

| | | |
|---|---|---|
| JP | 2005-17644 | 1/2005 |
| JP | 2005-274496 | 10/2005 |

OTHER PUBLICATIONS

M. Nagel, et al., "THz biosensing devices: fundamentals and technology", Journal of Physics: Condensed Matter 18, S601-S618, Institute of Physics Publishing (2006).

U.S. Appl. No. 12/300,791, filed Nov. 13, 2008, Inventors: Shintaro Kasai and Toshihiko Ouchi.

U.S. Appl. No. 12/682,248, filed Apr. 8, 2010, Inventors: Shintaro Kasai, Toshihiko Ouchi and Takeaki Itsuji.

U.S. Appl. No. 12/742,905, filed May 13, 2010, Inventors: Takashi Katagiri and Takeaki Itsuji.

* cited by examiner

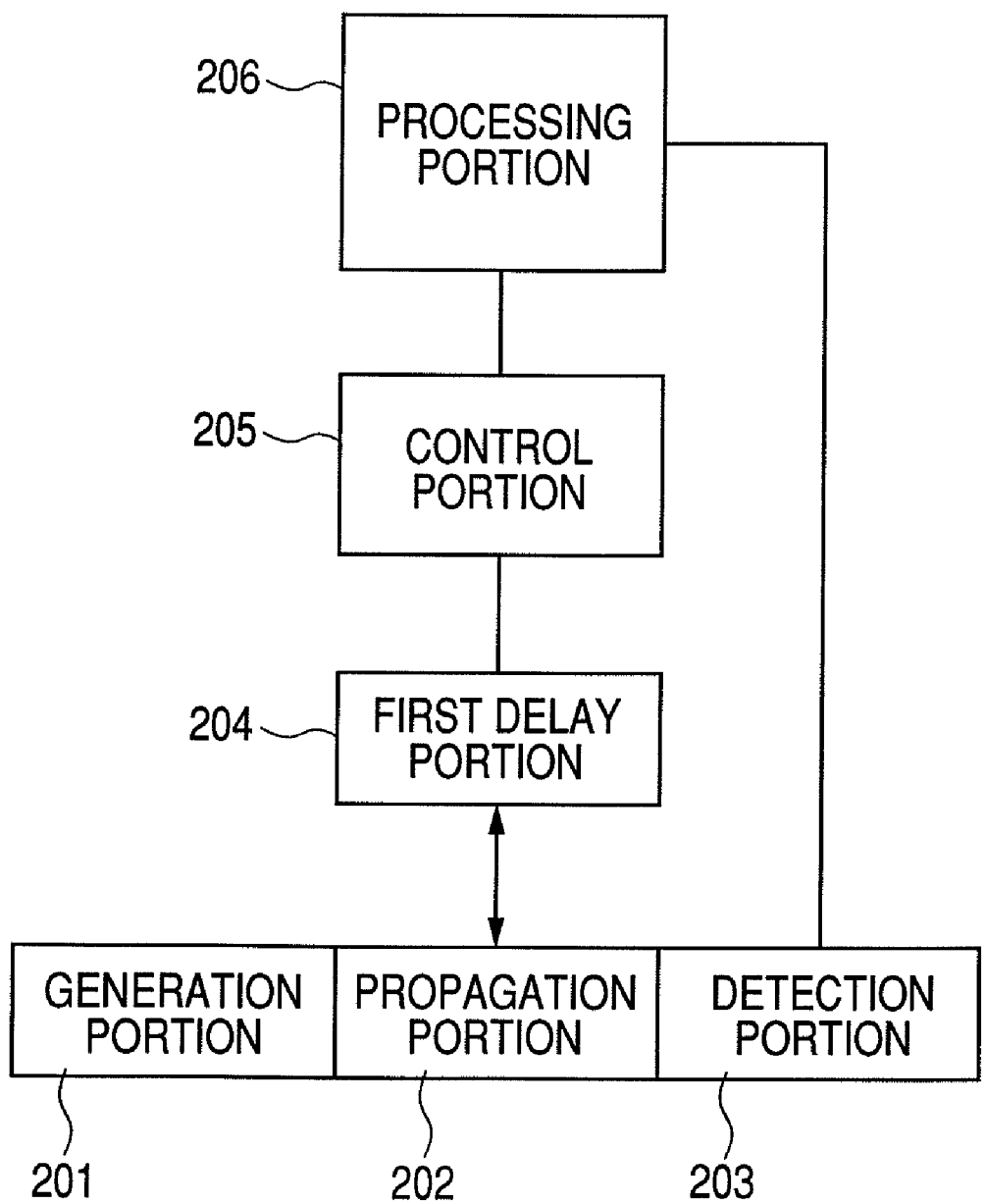

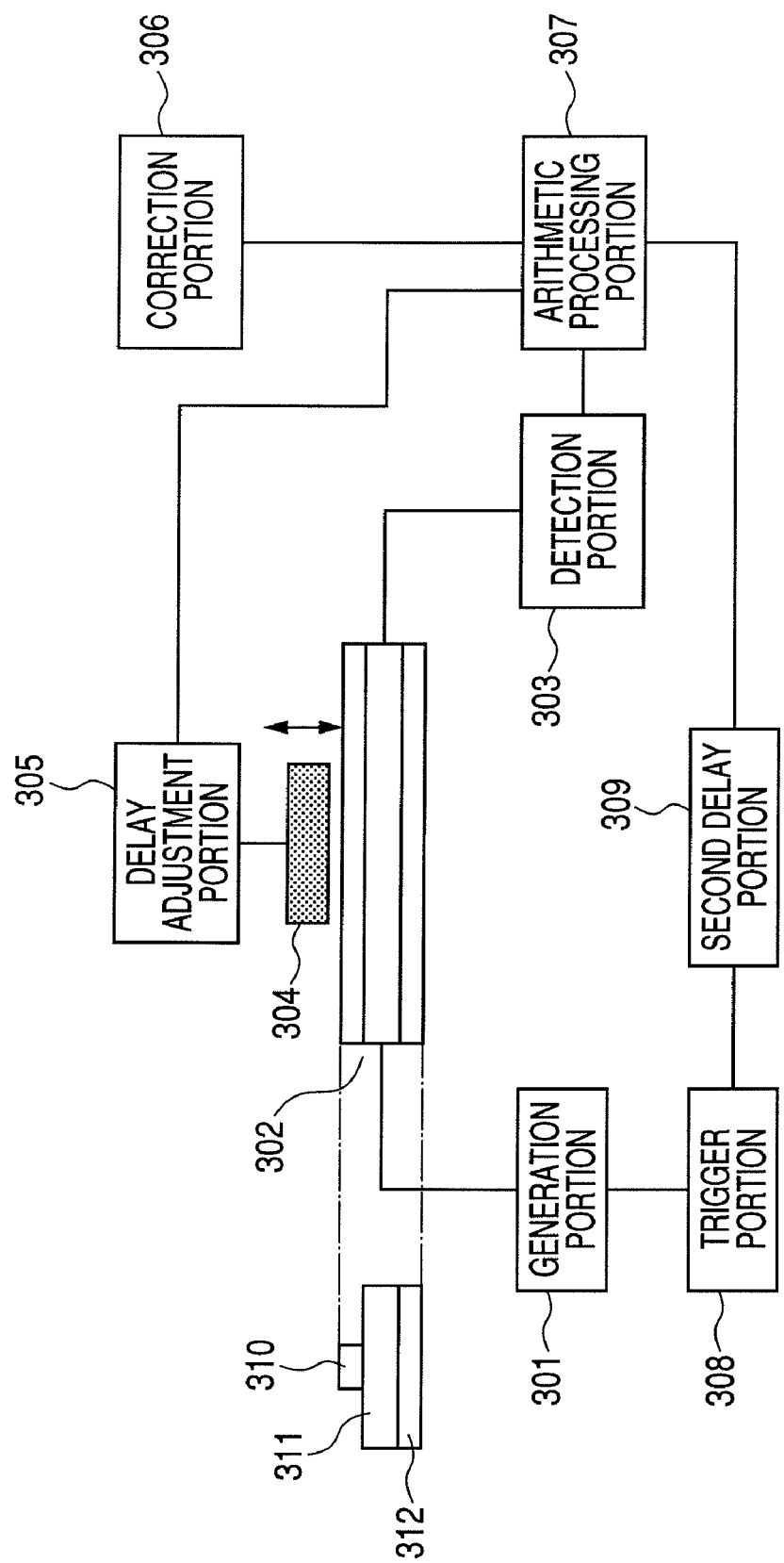

TERAHERTZ WAVE

TERAHERTZ WAVE

WAVEFORM INFORMATION ACQUISITION APPARATUS AND WAVEFORM INFORMATION ACQUISITION METHOD

TECHNICAL FIELD

The present invention relates to a waveform information acquisition apparatus and a waveform information acquisition method.

BACKGROUND ART

In a band of a terahertz wave, there exists a characteristic absorption band derived from the structures and states of various materials including biomolecules. Incidentally, the term "terahertz wave" employed herein refers to an electromagnetic wave having a frequency of from 30 GHz to 30 THz. An inspection technique for analyzing and identifying a material in a non-destructive manner has been developed by taking advantage of the characteristic as described above. Moreover, the application of the terahertz wave to a safe imaging technique in place of an X-ray or to a high-speed communication technology is expected.

As an analysis technique using the terahertz wave, there is a Terahertz Time Domain Spectroscopy (THz-TDS).

The THz-TDS is a measurement method for acquiring a temporal waveform of the terahertz wave (waveform of the terahertz wave represented with a time axis being taken as abscissa) which is transmitted through or reflected by a sample. A technology for acquiring physical properties of the sample by using information regarding an amplitude and a phase of the waveform acquired by this method is disclosed in Japanese Patent Application Laid-Open No. 2005-274496.

Moreover, a technology concerning an element, on which elements for generating and detecting the terahertz wave are integrated, is disclosed in Appl. Phys. Lett. 70, 2233, 1997. As an emission source of the THz wave used for the THz-TDS, a photoconductive film made of Low-Temperature grown GaAs (LT-GaAs) or the like is used. When a laser pulse beam is irradiated between electrodes on the photoconductive film, carriers instantaneously flow between the electrodes by photoexcitation. Then, a THz pulse proportional to a temporal differentiation of the carrier current is generated. Also on the detection side used for the THz-TDS, the photoconductive film is used. As is the case with the emission source, the laser pulse corresponding to an ultrashort pulse is used.

As described above, the Terahertz time domain spectroscopy is carried out by using the ultrashort pulse having a time width smaller than that of the terahertz wave. Specifically, a pulse laser having a pulse width of several tens of femtoseconds is used as the ultrashort pulse for sampling an amplitude (such as a photocurrent value) at a certain time on the temporal waveform of the terahertz wave. Then, the timing of irradiating light to the position at which the terahertz wave is emitted or detected is changed. As a result, the amplitude (such as the photocurrent value) of the terahertz wave can be acquired while the position on the temporal waveform at which each sampling is performed is being changed. As a result, the whole temporal waveform can be reproduced.

In order to change the timing of irradiation, a movable mirror for changing an optical path length of the ultrashort pulse is used as an optical delay system.

As described above, in order to acquire the temporal waveform of a terahertz wave, a method of using an optical delay system to change the timing of irradiating light to the position at which the terahertz wave is emitted or detected is known.

The present inventors have conducted extensive studies on a technology of acquiring a temporal waveform of a terahertz wave by using a technique different from the method described above, and have found that a temporal waveform can be reproduced even without using an optical delay system and accomplished the present invention.

DISCLOSURE OF THE INVENTION

It is, therefore, an object of the present invention to provide an apparatus and a method which are capable of acquiring information regarding a temporal waveform by a technique different from that described above using an optical delay system. It should be understood that the present invention does not exclude the combination of the above-mentioned conventional technique using the optical delay system and the novel technique.

According to a first aspect of the present invention, there is provided a waveform information acquisition apparatus for acquiring information regarding a temporal waveform of a terahertz wave, which includes:

a generation portion for generating a terahertz wave;

a detection portion for detecting waveform information of the terahertz wave; and a first delay portion for changing a time period from generation of the terahertz wave in the generation portion to detection of the terahertz wave as the waveform information of the terahertz wave in the detection portion, wherein the first delay portion is configured so as to change a propagation velocity of the terahertz wave generated by the generation portion, and wherein the waveform information of the terahertz wave detected by the detection portion and the propagation velocity are associated with each other for each terahertz wave generated by the generation portion.

According to a second aspect of the present invention, there is provided a waveform information acquisition apparatus including:

a generation portion for generating a terahertz wave;

a propagation portion for allowing the terahertz wave generated by the generation portion to propagate therethrough;

a detection portion for detecting waveform information of the terahertz wave;

a first delay portion for changing a propagation velocity of the terahertz wave generated by the generation portion in the propagation portion; and a control portion for controlling the first delay portion to change the propagation velocity of the terahertz wave propagating through the propagation portion, wherein information regarding a temporal waveform of the terahertz wave detected by the detection portion is acquired.

Further, according to a third aspect of the present invention, there is provided a waveform information acquisition method including:

allowing a terahertz wave to propagate;

acquiring waveform information of the terahertz wave propagating at a first propagation velocity;

changing a propagation velocity of the terahertz wave into a second propagation velocity;

acquiring waveform information of the terahertz wave propagating at the second propagation velocity; and acquiring information regarding a temporal waveform acquired from the waveform information of the terahertz wave propagating at the first propagation velocity and the terahertz wave propagating at the second propagation velocity.

Further, according to a fourth aspect of the present invention, there is provided a terahertz time domain spectroscopy method including:

generating a terahertz wave;

allowing the generated terahertz wave to propagate;

detecting information regarding the propagating terahertz wave; and constructing a temporal waveform of the terahertz wave from the detected information regarding the terahertz wave, wherein a propagation velocity of the terahertz wave is changed to acquire the temporal waveform.

According to the present invention, the propagation velocity (effective propagation distance) of the terahertz wave propagating through the propagation portion can be controlled. Thereby, a propagation time of the terahertz wave can be controlled. As a consequence, a temporal waveform of a terahertz wave can be acquired.

Further features of the present invention will become apparent from the following description of exemplary embodiments with reference to the attached drawings.

BRIEF DESCRIPTION OF THE DRAWINGS

FIG. 2 is a schematic view for illustrating a waveform information acquisition apparatus in accordance with a second embodiment.

FIG. 3 is a schematic view for illustrating a waveform information acquisition apparatus in accordance with one mode of the second embodiment.

BEST MODE FOR CARRYING OUT THE INVENTION

First Embodiment

Variation of Propagation Velocity

A first embodiment of the waveform information acquisition apparatus in accordance with the present invention will be described with reference to FIGS. 1A, 1B and 1C.

Like elements in the respective FIGURES have similar reference numbers.

Figure 1A:
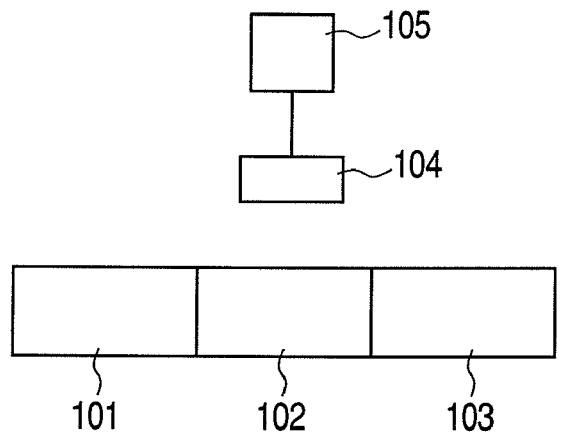
FIGS. 1A, 1B and 1C are schematic views for illustrating a waveform information acquisition apparatus in accordance with a first embodiment.

FIG. 1A is a schematic view illustrating a waveform information acquisition apparatus before a propagation velocity of a terahertz wave propagating through a propagation portion is changed.

Figure 1B:
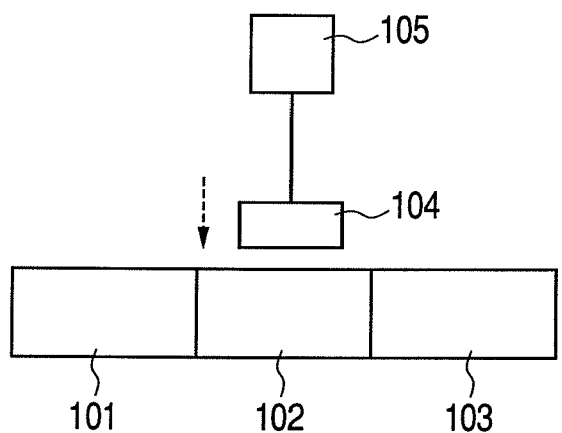

FIG. 1B is a schematic view illustrating the waveform information acquisition apparatus when the propagation velocity of the terahertz wave propagating through the propagation portion is changed.

A generation portion 101 generates the terahertz wave. As the generation portion 101, for example, there is included a generation portion which includes a carrier generation layer and uses the above-mentioned photoconductive film for generating the terahertz wave by application of an electric field to the carriers. Moreover, as the generation portion 101, a resonance tunnel diode having a structure, in which the electric field (or voltage) is applied to cause a resonance tunnel phenomenon, or the like can be used. However, the generation portion used in the present invention is not limited to those described above.

A propagation portion 102 allows the terahertz wave generated from the generation portion 101 to propagate therethrough. Here, the propagation portion 102 is a region through which the terahertz wave propagates. As the propagation portion 102, there is included, for example, a transmission line (microstrip line) configured to include a strip-shaped electrode or the like. Further, the propagation portion 102 may include air (gap) through which the terahertz wave propagates. However, the present invention is not limited to those described above.

A detection portion 103 detects waveform information of the terahertz wave. As the detection portion 103, the same structure as that of the generation portion described above can be used.

Here, the waveform information of the terahertz wave is a value of an amplitude at a certain time on a temporal waveform (waveform of the terahertz wave represented with a time axis being indicated as abscissa). It is sufficient that the waveform information is information of at least a part of the waveform.

A first delay portion 104 changes the propagation velocity (effective propagation distance) of the terahertz wave generated by the generation portion 101 in the propagation portion 102. For changing the propagation velocity, it is preferred to change a refractive index of the region (including the propagation portion 102) through which the terahertz wave propagates. The terahertz wave does not necessarily propagate only through the propagation portion 102, but propagates the region including the propagation portion 102.

The propagation velocity changes in proportion to an inverse number of the refractive index. For example, when the structure of the propagation portion 102 is partially open with respect to the propagating electromagnetic wave as in the case of the transmission line, the refractive index of the propagation portion 102 can be adjusted by adjusting the refractive index of the open portion. The refractive index of the propagation portion 102 is calculated as an average value including the refractive index of the open portion. Therefore, if the average refractive index can be adjusted by the first delay portion 104, the propagation velocity will be changed. Incidentally, the proportion of the open portion depends on the structure of the propagation portion 102. The selection of the propagation portion 102 having a large proportion of the open portion can increase a rate of change of the adjustable propagation velocity.

As means for changing the refractive index of the region through which the terahertz wave propagates, a mechanical means or an electrical means can be used.

As the mechanical means, for example, the position of the first delay portion 104 can be changed by using an actuator in order to change the distance from the propagation portion 102. The reason why the refractive index of the region through which the terahertz wave propagates can be changed by changing the position of the first delay portion 104 will be described later.

Moreover, as the electrical means, for example, a voltage applied to liquid crystal can be changed in order to change the orientation of liquid crystal molecules. When the liquid crystal molecules, each having the refractive index in a longitudinal direction different from that in a horizontal direction, are used, the refractive index perceived by the terahertz wave is changed by adjusting the orientation of the liquid crystal molecules with respect to the deflection of the terahertz wave propagating through the propagation portion 102. By using this phenomenon, the propagation velocity of the terahertz wave is changed. A specific example of changing the refractive index of the region through which the terahertz wave propagates by using the liquid crystal will be described later. Further, the propagation velocity (effective propagation distance) of the terahertz wave can also be changed by changing a concentration of a gas surrounding the region through which the terahertz wave propagates.

Here, when the terahertz wave is allowed to propagate in an electromagnetic field, the propagation characteristics of the terahertz wave are changed by changing an electric field or a magnetic field. In this case, when the rotation of polarization occurs, the frequency of the terahertz wave is changed to change the propagation velocity (phase velocity) which depends on the frequency.

As the first delay portion 104, any material can be used as long as it has a refractive index. For example, quartz can be used. A member made of polyethylene or polyolefin can also be used. Further, as the first delay portion 104, for example, the liquid crystal can be used. However, the present invention is not limited to those described above.

A control portion 105 controls the first delay portion 104 in order to change the propagation velocity of the terahertz wave propagating through the propagation portion 102.

The control portion 105 may control the refractive index of the region, through which the terahertz wave propagating through the propagation portion 102 propagates, in order to control the propagation velocity. However, the present invention is not limited thereto.

Here, the control of the first delay portion 104 includes, for example, the adjustment of the distance between the propagation portion 102 and the first delay portion 104. As an example of the adjustment of the distance, a change of the position of the first delay portion 104 while fixing the position of the propagation portion 102 can be given. It is to be noted that the adjustment of the distance according to the present invention is not limited thereto. The adjustment of the distance can be performed by using the mechanical means described above. This means can be adopted when, for example, the above-mentioned member (such as quartz) is used for the first delay portion 104.

The control of the first delay portion 104 also includes, for example, forming the first delay portion 104 of a liquid crystal or the like and adjusting the orientation of the liquid crystal molecules. The adjustment of the orientation can be performed by using the above-mentioned electrical means. This means can be adopted when, for example, a liquid crystal or the like is used for the first delay portion 104. This means can also be adopted when a colloidal solution is used for the first delay portion 104. As the colloidal solution, for example, a colloidal solution, in which charged particles obtained by coating ceramic particles with a resin material are dispersed in an insulating solution such as silicone oil, is used. When the refractive index of the insulating solution differs from that of the charged particles, the refractive index of the propagation portion 102 can be adjusted by adjusting the density of the charged particles distributed in a range covered by an electromagnetic field of a terahertz wave propagating through the propagation portion 102. As a result, the propagation velocity of the terahertz wave can be adjusted. In this case, by adjusting the voltage applied to the first delay portion 104 (or by adjusting current), the dispersion of colloids in the colloidal solution can be adjusted. Incidentally, when the frequency of the voltage (or current) used for adjusting the dispersion of the colloids is distinguished from that of the terahertz wave, the influence of a signal for the adjustment on the terahertz wave propagating through the propagation portion 102 can be eliminated.

As described above, the control portion 105 can control the refractive index of the region through which the terahertz wave propagating through the propagation portion 102 propagates.

With the configuration described above, the propagation time of the terahertz wave can be changed. Moreover, the sampling position on the time axis, at which the temporal waveform of the terahertz wave is sampled in the detection portion 103, can be changed. Further, since the propagation time of the terahertz wave can be controlled, each sampling position can be controlled. By sequentially recording a signal for each sampling position, the whole temporal waveform of the terahertz wave can be constructed.

With the structure of this embodiment, information regarding the temporal waveform of the terahertz wave, which is detected by the detection portion 103, can be acquired. Here, the expression "information regarding temporal waveform" herein employed includes information regarding the amplitude and phase of the terahertz wave and the like.

(Mode in which the Propagation Portion Includes a Gas Such as Air)

The case where the propagation portion 103 included in the waveform information acquisition apparatus according to the embodiment described above includes a gas such as air will be described with reference to FIG. 1C.

Figure 1C:
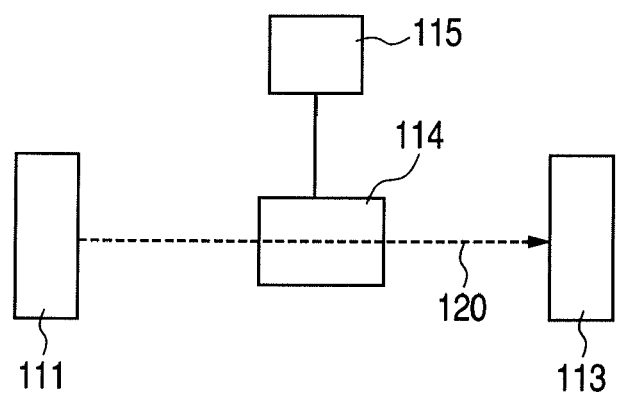

FIG. 1C is a schematic view illustrating the waveform information acquisition apparatus for acquiring the information regarding the temporal waveform of the terahertz wave.

A generation portion 111 generates the terahertz wave. The generation portion 111 may be a semiconductor having photoconductivity (having a single-layered structure; also referred to as a photoconductive film) such as low-temperature grown GaAs (LT-GaAs), InGaAs, or AlGaAs. Furthermore, the generation portion 111 may be a structure including the semiconductor having the photoconductivity (having a multi-layered structure). The structure is a diode structure (structure provided with a rectification property) configured to include the semiconductor having a band gap energy smaller than a photon energy of excitation light. For example, a p-i-n diode structure, a metal-i-n diode structure, a metal-i-metal diode structure, a Schottky barrier diode structure or the like can be used. The diode structures described above can reduce a current which is made to flow by the carriers generated by irradiation of the excitation light upon application of a reverse bias to an element. Therefore, even when the resistance of the generation portion 111 is small, the electric field can be efficiently applied to the carriers. Although, for example, InGaAs having a smaller resistance than that of LT-GaAs may be used as a material of an i-layer here, the present invention is not limited thereto. Moreover, a resonance tunnel diode, a semiconductor superlattice, a superconductor or the like may be used for the generation portion 111.

Furthermore, a detection portion 113 detects the waveform information of the terahertz waveform. The same structure as that of the generation portion 111 described above can be used for the detection portion 113.

Here, the waveform information of the terahertz wave refers to, for example, a value of amplitude at a certain time on the temporal waveform (waveform of the terahertz wave represented with a time axis being taken as abscissa). It is sufficient that the waveform information is information of at least a part of the waveform.

A first delay portion 114 changes a time period from the generation of the terahertz wave in the generation portion 111 to the detection of the terahertz wave as the waveform information of the terahertz wave in the detection portion 113. The first delay portion 114 is a mechanism for performing the terahertz time domain spectroscopy (THz-TDS) described above. As a specific structure of the first delay portion 114, a mode such as Example 4 described later can be used in addition to the embodiment described above. It is sufficient that the first delay portion 114 is configured to change the propagation velocity of the terahertz wave generated by the generation portion 111. The delay portion 114 may also be configured to change the refractive index of the region through which the terahertz wave generated by the generation portion 111 propagates.

Here, the first delay portion 114 may be configured to include a member having a refractive index different from that of the region through which the terahertz wave generated by the generation portion 111 propagates. Furthermore, the first delay portion 114 may also be configured to change a relative positional relation between the member and the region (Examples 1 and 2). The first delay portion 114 may also be configured to change the rate at which the member occupies the region (Example 4).

For each terahertz wave (or each different terahertz wave) generated by the generation portion 111, the waveform information of the terahertz wave detected by the detection portion 113 and the propagation velocity are associated with each other. The term "different terahertz wave" herein employed means the relation between a first terahertz wave and a second terahertz wave different from the first terahertz wave of the terahertz waves generated by the generation portion 111.

As described above, the terahertz time domain spectroscopy can be performed by a technology different from that of the background art to acquire the information regarding the temporal waveform of the terahertz wave. The information regarding the temporal waveform includes information regarding the amplitude and phase of the terahertz wave.

As described for the above-mentioned embodiment, a control portion 115 for controlling the first delay portion 114 may also be provided. Incidentally, reference numeral 120 denotes a terahertz wave that propagates through the first delay portion 114.

Here, the terahertz time domain spectroscopy is a technique for constructing a temporal waveform of the terahertz wave from the detected information regarding the terahertz wave. This embodiment describes a technology of changing the propagation velocity of the terahertz wave to obtain the temporal waveform. The propagation velocity can be changed by changing the effective propagation distance or an optical distance (product of the refractive index and a spatial distance). At this time, it is desirable that the spatial distance be constant.

(Waveform Information Acquisition Method)

A waveform information acquisition method according to this embodiment includes at least Steps 1) to 5) below.

1) Step of allowing a terahertz wave to propagate;
2) Step of acquiring waveform information of the terahertz wave propagating at a first propagation velocity;
3) Step of changing the propagation velocity of the terahertz wave to a second propagation velocity;
4) Step of acquiring waveform information of the terahertz wave propagating at the second propagation velocity; and
5) Step of acquiring information regarding a temporal waveform acquired from the waveform information of the terahertz waves propagating at the first propagation velocity and the second propagation velocity.

Incidentally, for the information regarding the temporal waveform, the whole temporal waveform may be constructed from the waveform information. Furthermore, for the information regarding the temporal waveform, the whole time information may be constructed from information at several points on the temporal waveform. Moreover, the temporal waveform may not be required to be constructed.

Second Embodiment

Correction of Change in Intensity or Pulse Width

A second embodiment of the waveform information acquisition apparatus according to will be described referring to FIG. 2.

A generation portion 201 generates a terahertz wave. A propagation portion 202 allows the terahertz wave generated by the generation portion 201 to propagate therein. A detection portion 203 detects waveform information of the terahertz wave. A first delay portion 204 changes the propagation velocity in the propagation portion 202 of the terahertz wave generated by the generation portion 201. A control portion 205 controls the first delay portion 204 to change the propagation velocity of the terahertz wave propagating through the propagation portion 202. The description made for the above-mentioned embodiment as such applies to these constituents (201 to 205).

The configuration shown in FIG. 2 differs from that of the first embodiment in that a processing portion 206 is additionally provided.

The processing portion 206 corrects the information regarding the temporal waveform of the terahertz wave detected by the detection portion 203. For example, the information may be corrected so as to provide the shape of the temporal waveform taken before the propagation velocity of the terahertz wave propagating through the propagation portion 202 is changed.

With a change in the refractive index of the region through which the terahertz wave propagates, the shape of the temporal waveform of the terahertz wave is distorted. Specifically, the intensity or pulse width of the terahertz wave varies.

Here, the processing portion 206 may be configured to include an arithmetic processing portion and a correction portion. The arithmetic processing portion and the correction portion will be described later.

By using the processing portion 206, the distortion of the waveform that affects the propagation characteristics of the terahertz wave, which is caused by the first delay portion 204, can be corrected with a correction value prepared in advance.

Hereinafter, a specific example of a method of correcting the distortion of the waveform of the terahertz wave will be described. Incidentally, the correction value can be obtained, for example, by using a second delay portion constituted of the optical delay system already described above and the like. It is needless to say that, when a database for the correction values is completed, the second delay portion is not necessarily required to be used.

FIG. 3 is a schematic diagram for illustrating one mode of the second embodiment of the waveform information acquisition apparatus in accordance with the present invention.

(Generation Portion and Detection Portion for Terahertz Wave)

A generation portion 301 generates a terahertz wave. A detection portion 303 detects the terahertz wave. Incidentally, these portions each do not necessarily need to be configured independently of each other and may together be configured as one portion having both functions of generation and detection.

Each of the generation portion 301 and the detection portion 303 is operated by a trigger signal from a trigger portion 308. The trigger signal output to the detection portion 303 is delayed in time by a second delay portion 309 with respect to the trigger signal output to the generation portion 301. By adjusting the second delay portion 309, the time delay can be adjusted. The adjustment of the time delay is performed, for example, by changing the optical path length of the trigger signal output to the detection portion 303. The adjustment may be performed by the arithmetic processing portion 307 or by using a driver (not shown), and therefore, is not particularly limited.

(Terahertz Time Domain Spectrometry: TDS)

Since a signal of a terahertz wave has a high response speed, it is difficult to acquire the signal in real time. Therefore, in many cases, the terahertz wave is sampled by using a trigger signal to acquire a response waveform. For the trigger signal, a pulse shape of several tens to several hundreds of femtoseconds is used in many cases. At this time, the detection portion 303 operates for a time period during which the trigger signal is present, that is, for several tens to several hundreds of femtoseconds. The time period during which the detection portion 303 operates is sufficiently smaller with respect to the temporal waveform of the terahertz wave. At this time, for the terahertz wave detected by the detection portion 303, a value at an instant at which the trigger signal is present is measured. This instantaneous value is a value which corresponds to the electric field intensity of the terahertz wave.

For example, the time at which the trigger signal reaches the detection portion 303 is delayed, and the instantaneous value (electric field intensity of the terahertz wave) of the terahertz wave which reaches the detection portion 303 is recorded each time. Thereby, the temporal waveform (waveform of the terahertz wave represented with a time axis being indicated as abscissa) of the terahertz wave can be constructed.

Here, the amount of change (for example, optical path length of a trigger signal output to the detection portion 303) of the second delay portion 309 from a certain reference value (0 second when converted into time) is converted into time. The position (amount of delay) of the second delay portion 309 is adjusted so as to achieve a predetermined observation time to thereby adjust the time at which the trigger signal reaches the detection portion 303. The instantaneous value of the terahertz wave (electric field intensity of the terahertz wave) at the predetermined observation time is detected by the detection portion 303.

Incidentally, the trigger signal is not limited to the light irradiation to the generation portion 301 and the detection portion 303. For example, an electric field (or voltage) may be applied to a structure using the resonance tunnel phenomenon in order to generate a terahertz wave.

(Transmission Line Delay Device)

Here, a transmission line delay device is constituted by a propagation portion 302, a first delay portion 304, and a delay adjustment portion 305.

A terahertz wave generated in the generation portion 301 propagates through the propagation portion 302. The propagation portion 302 is a waveguide which includes at least a strip-shaped first electrode 310 (see the side view shown in the leftmost part of FIG. 3). Here, an example in which a microstrip line including a dielectric 311 interposed between the first electrode 310 and a flat plate-shaped reference electrode 312 (electrode for defining an electric potential serving as a reference of the electric field) is adopted is described. However, the structure of the waveguide is not limited thereto. For example, a coplanar waveguide or a coplanar strip line can also be adopted.

(First Delay Portion)

The first delay portion 304 is a member having a certain refractive index (member such as quartz or a polyethylene member). In this embodiment, the first delay portion 304 is located at a position perpendicular to the longitudinal direction of the first electrode 310 constituting the propagation portion 302. In the present invention, however, the first delay portion need not necessarily be perpendicular to the longitudinal direction of the first electrode 310.

The first delay portion 304 is located at a position which is apart by a certain distance from the propagation portion 302. Furthermore, the delay adjustment portion 305 plays the role of adjusting the first delay portion 304 to thereby adjust the distance between the first delay portion 304 and the propagation portion 302. By controlling the distance between the propagation portion 302 and the first delay portion 304, a change in refractive index of the region through which the terahertz wave propagates (change in refractive index distribution state) can be controlled. Thereby, the change in effective propagation distance (electrical length) of the terahertz wave propagating through the propagation portion 302 can be controlled, thereby controlling the change in time period in which the terahertz wave reaches the detection portion 303 (propagation time).

Although in this embodiment, the distribution state of the refractive index of the propagation portion 302 is adjusted by the distance between the first delay portion 304 and the propagation portion 302, the adjustment of the distribution state of the refractive index of the propagation portion 302 is not limited thereto. For example, the first delay portion 304 may be constituted of a member which is capable of changing the refractive index by using the electrical means, such as a liquid crystal and an electrode for using the electrical means. In this case, the delay adjustment portion 305 functions as a control portion for changing the refractive index of the first delay portion 304 by using the electrical means.

Moreover, there may be adopted a configuration which changes the refractive index of the first delay portion 304 by the electrical means and adjust the distance from the propagation portion 302 to thereby change the refractive index distribution.

An arithmetic processing portion 307 is a portion that refers to an output signal from the detection portion 303 to construct a temporal waveform of the terahertz wave. Specifically, for a trigger signal that reaches the detection portion 303, a change in time period in which the terahertz wave reaches the detection portion 303 and a change in output of the detection portion 303 are sequentially recorded. Thereby, the temporal waveform of the terahertz wave can be constructed.

(Change in Propagation Velocity Caused by First Delay Portion)

Figure 4:
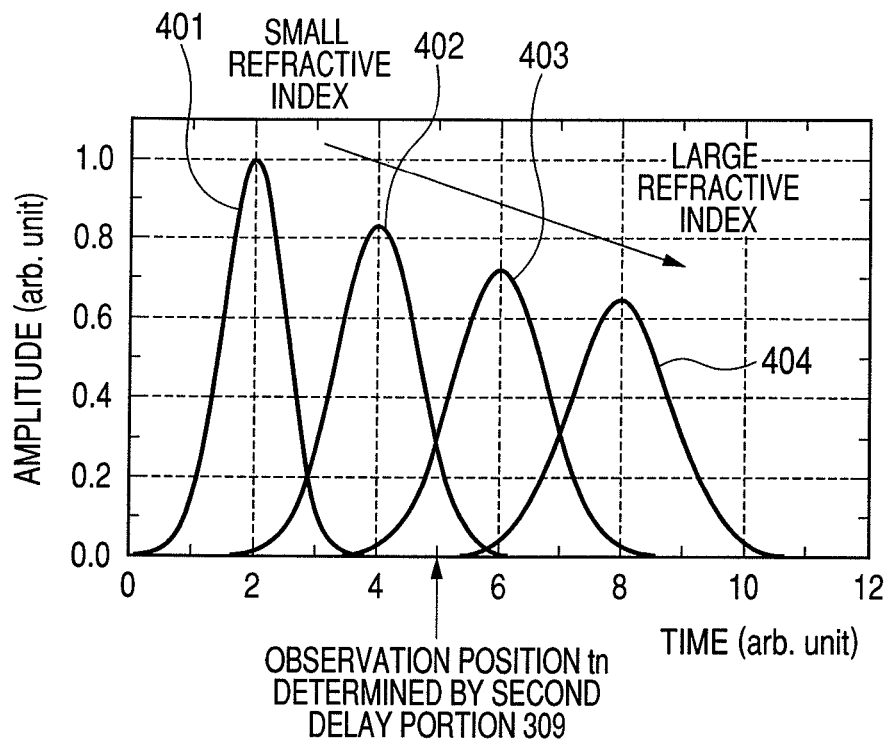
FIG. 4 is a graphical representation for illustrating a change in a terahertz wave propagating through a propagation portion when a first delay portion is adjusted.

Temporal waveforms 401, 402, 403 and 404 illustrated in FIG. 4 are temporal waveforms of the terahertz waves detected by the detection portion 303 by adjusting the position (amount of delay) of the second delay portion 309. The differences between the respective spectra of the temporal waveforms are generated by adjusting the first delay portion 304 to thereby change the refractive index distribution of the propagation portion 302.

For example, the temporal waveform 401 is acquired as follows. Specifically, in a state where the distance between the first delay portion 304 and the propagation portion 302 is fixed to a certain distance x1, the trigger signal is swept (delayed in time) in the second delay portion 309. Similarly, the temporal waveform 402 is a temporal waveform of the terahertz wave acquired in a state where the distance is x2.

The distance between the propagation portion 302 and the first delay portion 304 is controlled by the delay adjustment portion 305 to thereby increase the refractive index of the propagation portion 302 through which the terahertz wave propagates.

Here, when the propagation portion includes, for example, a dielectric, the terahertz wave propagates not only through the dielectric but also outside of the dielectric (for example, in air). Therefore, by reducing the distance between the first delay portion 304 (for example, a material having a larger dielectric constant than that of air) and the propagation portion 302, the dielectric constant of the region through which the terahertz wave propagates is increased in total. Incidentally, the increase in dielectric constant means an increase in refractive index.

It can be seen from FIG. 4 that by changing the refractive index distribution of the propagation portion 302, the temporal waveform of the terahertz wave transits from that indicated by reference numeral 401 to that indicated by reference numeral 404. At this time, it is observed that the propagation velocity of the propagating terahertz wave is reduced.

(Apparatus Operation)

Hereinafter, an operation of the waveform information acquisition apparatus of this embodiment will be described.

In this embodiment, the propagation velocity (effective propagation distance) of the terahertz wave is changed to acquire the temporal waveform of the terahertz wave. In this manner, the time period until the terahertz wave reaches the detection portion 303 is changed. Then, during the observation time (or at the observation position) predetermined by the second delay portion 309, a signal changing with the change in propagation velocity (effective propagation distance) of the terahertz wave is sequentially detected to acquire the temporal waveform of the terahertz wave.

For example, in FIG. 4, an observation time tn is determined at a position of 5 picoseconds. Then, the position of the second delay portion 309 is adjusted such that the observation position tn is 5 picoseconds. In this state, the first delay portion 304 is adjusted to thereby change the propagation velocity (effective propagation distance) of the terahertz wave propagating through the propagation portion 302. Thereby, the observation time of the temporal waveform of the terahertz wave can be changed. Specifically, the adjustment of the first delay portion 304 can temporally sweep (temporally delay) the temporal waveform of the terahertz wave.

(Arithmetic Processing Portion)

The arithmetic processing portion 307 causes the delay adjustment portion 305 to adjust the first delay portion 304 in a state where the position of the second delay portion 309 is fixed at the observation time tn (for example, 5 picoseconds). Referring to the amount of adjustment by the delay adjustment portion 305 and the output from the detection portion 303, the temporal waveform of the terahertz wave is constructed by the arithmetic processing portion 307.

Figure 5:
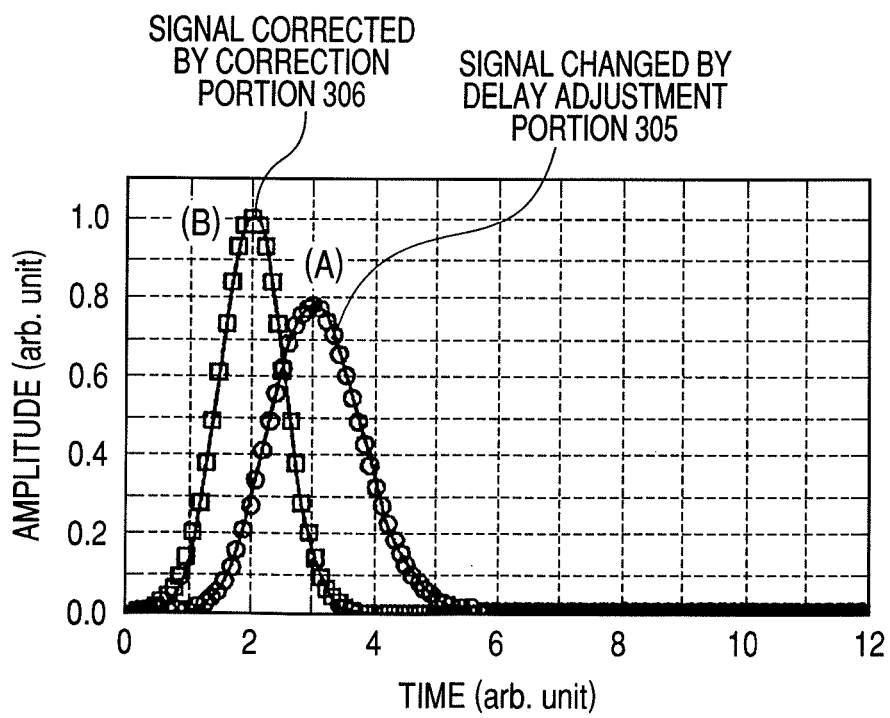
FIG. 5 is a graphical representation for illustrating a temporal waveform of the terahertz wave constructed in an arithmetic processing unit.

A temporal waveform of the terahertz wave constructed by the arithmetic processing portion 307 is illustrated as a temporal waveform (A) in FIG. 5. A temporal waveform (B) in FIG. 5 is a temporal waveform of the terahertz wave which is desired to be acquired (specifically, temporal waveform free from distortion due to a change in refractive index). The temporal waveform (B) of FIG. 5 is based on the temporal waveform 401 illustrated in FIG. 4 as a reference waveform (waveform which is not affected by the transmission line delay device). Incidentally, the temporal waveform 401 is a temporal waveform having a peak value at 2 picoseconds.

The temporal waveform (A) of FIG. 5 shows a change in intensity at the observation position tn, which is recorded when the propagation speed (effective propagation distance) of the propagating terahertz wave is changed. Thus, the temporal waveform (A) shows the instantaneous value of the terahertz wave detected by the detection portion 303, which is recorded when the refractive index of the propagation portion 304 is sequentially increased in FIG. 4 (in a direction indicated by an arrow of FIG. 4). At this time, the instantaneous value of the terahertz wave observed at the observation position tn transits from the observation position tn toward the top of a pulse with respect to the reference waveform. This transition corresponds to a sweep (temporal delay) of the time axis illustrated in FIG. 4 in a negative direction. Therefore, the temporal waveform (A) illustrated in FIG. 5, which is observed at the observation position tn, is inverted with respect to the temporal waveform (B) as the reference waveform illustrated in FIG. 5.

Here, peak values of the pulses (A) and (B) illustrated in FIG. 5 are offset with respect to each other on the time axis. The offset in time corresponds to an offset in propagation time. This represents a time delay caused by a change in the propagation velocity of the propagating terahertz wave.

Incidentally, the above description has been made by taking, as an example, the operation in a direction in which the temporal waveform of the terahertz wave is delayed (in a positive direction on the time axis). However, a mode of the operation in a negative direction on the time axis is not excluded. In this case, the state of the inverted relation between the temporal waveforms (A) and (B) illustrated in FIG. 5 is cancelled.

(Correction Portion)

Furthermore, along with the change in refractive index of the region including the propagation portion 302, the shape of the temporal waveform of the terahertz wave is distorted. Specifically, the intensity and pulse width of the terahertz wave change.

Here, the reason for the distortion of the shape of the temporal waveform of the terahertz wave can be considered as follows. For example, when the effective propagation distance of a terahertz wave changes, the energy of the terahertz wave, which is lost by a conductor or the dielectric, increases. Moreover, along with a change in effective propagation distance of a terahertz wave, differences between the propagation velocities of respective frequency components, which is caused by the influence of the dispersion, becomes remarkable, resulting in increase in the pulse width of the terahertz wave. Moreover, the shape of the temporal waveform of the terahertz wave is influenced by the characteristics of the loss and the characteristics of the dispersion of the means for generating a change in refractive index of the terahertz wave.

A correction value for correcting the distortion of the shape is stored in a correction portion 306. By using the correction value, the temporal waveform taken before the shape of the temporal waveform is distorted is reconstructed from the temporal waveform constructed in the arithmetic processing portion 307.

The temporal waveform (A) of FIG. 5 contains the influence of the propagation characteristics such as the loss and dispersion in the propagation portion. Therefore, the temporal waveform (A) differs from the reference waveform (B) illustrated in FIG. 5 in intensity and pulse width. Therefore, the arithmetic processing portion 307 performs an operation of reconstructing the constructed temporal waveform (A) into the temporal waveform (B) illustrated in FIG. 5. At this time, the correction value in the correction portion 306 is referred to.

Figure 6:
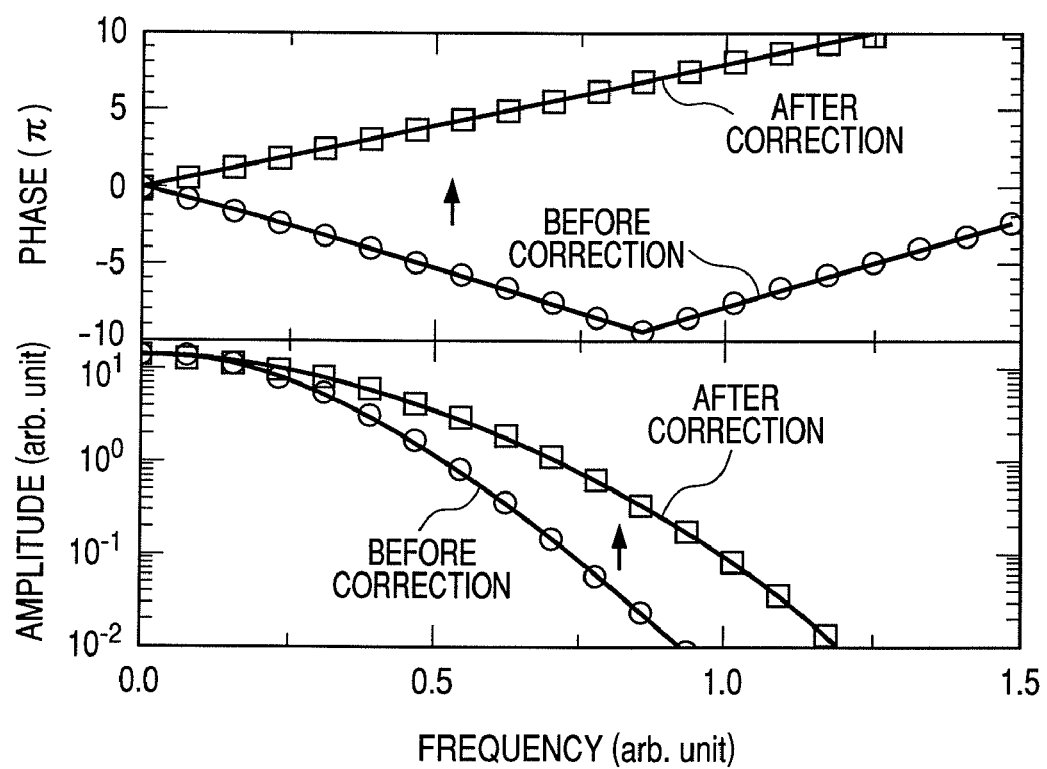
FIG. 6 is a graphical representation for illustrating an operation of a correction portion.

In the correction portion 306, the correction value for correcting the intensity and the phase for each frequency is stored for a predetermined observation position. Here, FIG. 6 shows an example of a table for correction, which is stored in the correction portion 306. Frequency information before the correction, which is illustrated in FIG. 6, corresponds to the temporal waveform (A) illustrated in FIG. 5. Frequency information after the correction, which is illustrated in FIG. 6, corresponds to the temporal waveform (B) illustrated in FIG. 5. The frequency information can be obtained by performing a Fourier transform on each temporal waveform.

Here, as the frequency information before the correction, a waveform which is subjected to signal processing in the following manner is used. Specifically, the peak position of the temporal waveform (A) illustrated in FIG. 5 is aligned with that of the reference waveform (B) illustrated in FIG. 5, and then, the waveform is inverted about the peak position.

Since the intensity and pulse width of the temporal waveform (A) illustrated in FIG. 5 differ from those of the temporal waveform (B) illustrated in FIG. 5, a difference also exists between the frequency information before and after the correction, which are illustrated in FIG. 6. The table for correction such as illustrated in FIG. 6 may be prestored in the correction portion 306 for each observation position tn. Specifically, for example, when the observation position is at 5 picoseconds, the intensity is tripled and the phase is advanced by 9.2 π for a frequency component of 0.5 THz. As a result, the temporal waveform can be corrected. The arithmetic processing portion 307 reconstructs the acquired temporal waveform of the terahertz wave, referring to the table corresponding to the observation position tn.

Though the table for correction prepared in the correction portion 306 can be obtained in advance by an actual measurement, the table for correction can also be obtained by a calculation. By referring to the table for a certain observation position, which is obtained by the actual measurement, a table for another observation position, which has not been measured, may be calculated to be complemented.

(Difference from General THz-TDS)

As described above, in the Terahertz time domain spectroscopy (THz-TDS), the temporal waveform of the terahertz wave is acquired. On the acquisition of the temporal waveform, a method of changing timing of irradiating light to the position of generation and the position of detection of the terahertz wave is generally used. When the above-mentioned method is used, the propagation time of the terahertz wave is not changed. Moreover, when the above-mentioned method is used, it is desirable to keep the propagation time of the terahertz wave constant.

In the present invention, the timing of irradiating light to the position of generation and the position of detection of the terahertz wave is not changed. It is desirable that the timing be constant in the present invention. In the present invention, the temporal waveform of the terahertz wave is acquired by changing the propagation time of the terahertz wave. In order to change the propagation time, the propagation velocity or the effective propagation distance (electrical length) is changed.

Here, the effective propagation distance is now described. When the expression of v (propagation velocity)=c (light velocity)/n (refractive index) is substituted into the expression of t (propagation time)=x (propagation distance)/v (propagation velocity), t=nx/c is obtained. As is clearly seen from the expressions described above, to set n variable has the following two meanings. Specifically, to set n variable means that v is set variable and that nx(=y) is set variable. The value of y is the effective propagation distance. Incidentally, the foregoing description has been made on the assumption that the terahertz wave propagates in a free space.

In the present specification, description is also made on the assumption that when the propagation velocity is changed, the effective propagation distance is constant (specifically, a distance that the terahertz wave actually propagates is constant). Description is also made on the assumption that when the effective propagation distance is changed, the propagation velocity is constant (specifically, the velocity at which the terahertz wave propagates is the light velocity). However, to set the effective propagation distance or the propagation velocity constant is not essential to the present invention. The essence of the present invention resides in the control of the propagation time.

Hereinafter, examples are described with reference to the accompanying drawings.

EXAMPLES

Example 1

Adjustment of Distance Between First Delay Portion and Propagation Portion

Example 1 is described with reference to FIG. 7.

Figure 7:
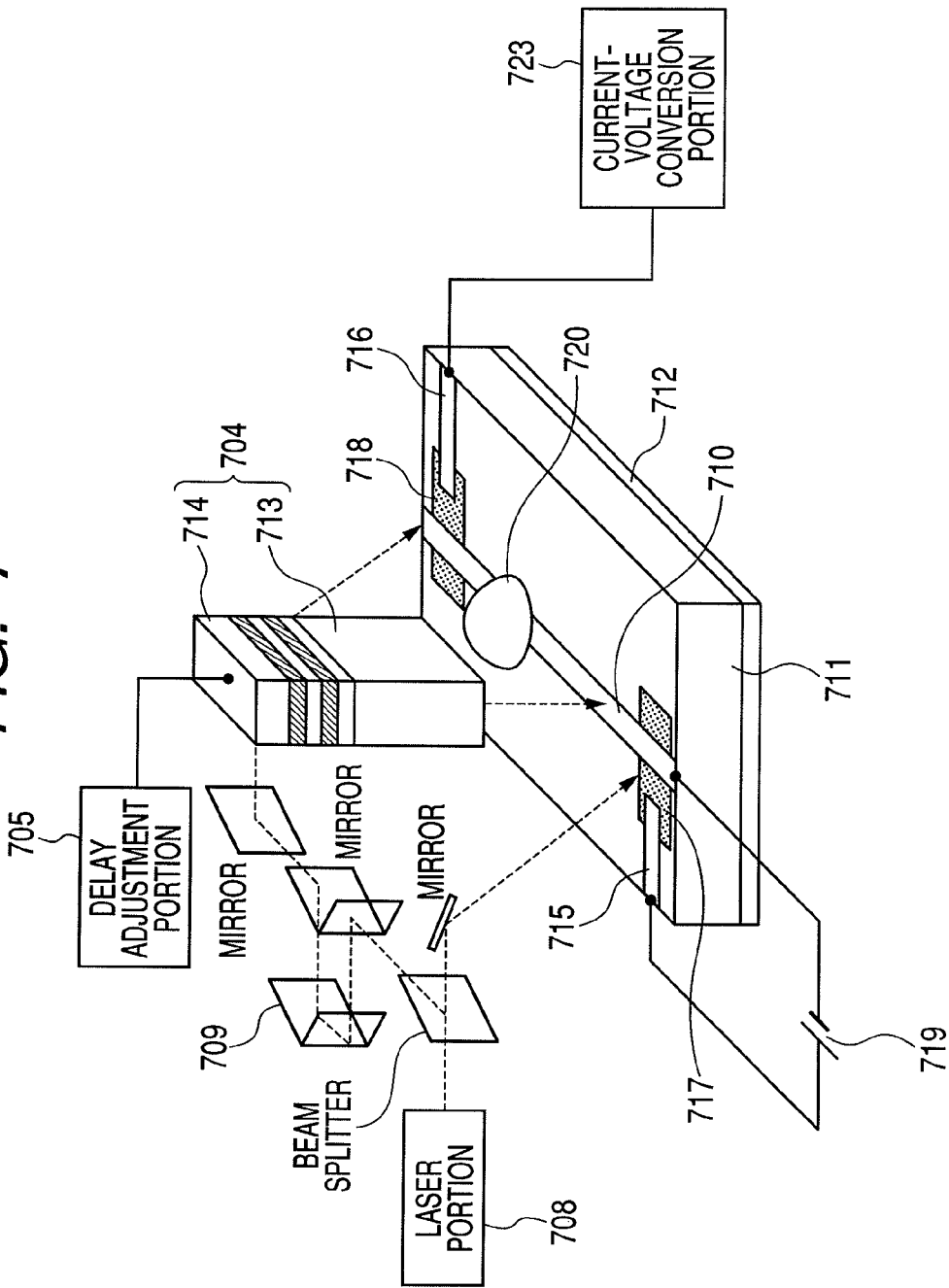
FIG. 7 is a schematic view for illustrating a waveform information acquisition apparatus in accordance with Example 1.

FIG. 7 is a schematic view for illustrating the waveform information acquisition apparatus of Example 1.

As a propagation portion, a microstrip line including a first electrode 710, a dielectric 711, and a reference electrode 712 is used. The propagation portion is formed on a silicon (Si) substrate (not illustrated).

The first electrode 710 is a conductor obtained, for example, by stacking a layer of titanium (Ti) in a thickness of 500 Å and a layer of gold (Au) in a thickness of 3,000 Å. The line width of the first electrode 710 is 5 μm. The reference electrode 712 is a flat plate-shaped conductor formed on the Si substrate. The reference electrode 712 provides a reference electric potential to each of the portions constituting the element. The structure of the conductor is the same as that of the first electrode 710.

For the dielectric 711, benzocyclobutene (BCB) is used. However, the material of the dielectric 711 is not limited thereto, and a resin material such as a polyethylene or polyolefin material can be used. A material having a small loss with respect to the terahertz wave is desirable. Furthermore, as the dielectric 711, a semiconductor material such as semi-insulating silicon (SI—Si) can be used. Moreover, as such a semiconductor material, the same material as that of a carrier generation layer can also be used. The film thickness of the dielectric 711 is 3 μm.

A laser portion 708 is used as the trigger portion. By the laser portion 708, the generation portion configured including a first carrier generation layer 717 is irradiated with a laser light to be driven. By the laser portion 708, the detection portion configured including a second carrier generation layer 718 is also irradiated with a laser light to be driven. Here, the laser light irradiated to the first carrier generation layer 717 is referred to as pump light, whereas the laser light irradiated to the second carrier generation layer 718 is referred to as probe light. For the laser portion 708, a titanium sapphire laser having a pulse width of 50 femtoseconds, a center wavelength of 800 nm, and a repetition frequency of 76 MHz is used.

The laser light output from the laser portion 708 is split by a beam splitter. Furthermore, through a mirror and a second delay portion 709, the laser lights are irradiated to the first carrier generation layer 717 and the second carrier generation layer 718.

As the second delay portion 709, an optical delay system which includes the combination of a retroreflector and a return optical system and changes the optical path length of an ultrashort pulse with an actuator is employed.

Here, the generation portion is constituted by the first carrier generation layer 717, the first electrode 710, the second electrode 715, and a bias application portion 719. For the first carrier generation layer 717, low-temperature grown gallium arsenide (LT-GaAs) is used. On a semi-insulating gallium arsenide (SI—GaAs) substrate (specific resistance: more than $1 \times 10^7 \Omega \cdot cm$), LT-GaAs is fabricated by molecular beam low-temperature epitaxial growth (at 250° C.) and is peeled off from the Si—GaAs substrate for use. The thickness of the first carrier generation layer 717 is 2 μm. The second electrode 715 is a conductor obtained, for example, by stacking a layer of Ti with a thickness of 500 Å and a layer of Au with a thickness of 3,000 Å, as is the case with the first electrode 710. The line width of the second electrode 715 is 10 μm.

The first electrode 710 and the second electrode 715 are provided on the first carrier generation layer 717 with a certain gap therebetween. The gap is 5 μm. The bias application portion 719 is a portion for applying a bias to the gap, and applies a bias at 10 V to the gap. The pump light output from the laser portion 708 is irradiated to the gap to generate carriers. The bias is applied to the carriers by the bias application portion 719 to accelerate the carriers. Thereby, an electromagnetic wave is generated and used as a terahertz wave. The terahertz wave is coupled to the first electrode 710, and propagates through the propagation portion.

The structure of the detection portion is the same as that of the generation portion. The detection portion is constituted by the second carrier generation layer 718, the first electrode 710, a third electrode 716, and a current-voltage conversion portion 723. The second carrier generation layer 718 and the third electrode 716 have the same structures as those of the first carrier generation layer 717 and the second electrode 715 of the generation portion, respectively. The current-voltage conversion portion 723 converts a current flowing through the third electrode 716 into a voltage, and then amplifies the voltage.

The probe light output from the laser portion 708 is irradiated to a gap between the first electrode 710 and the third electrode 716. The gap is the same as that in the generation portion, and therefore, is 5 μm. The probe light causes the carriers to be generated in the gap from the second carrier generation layer 718. The generated carriers are fluctuated by an electromagnetic field of the terahertz wave propagating from the propagation portion. A current signal involved in the fluctuation of the carriers is transmitted to the third electrode 716. The current-voltage conversion portion 723 detects the current signal. Here, the detected signal is an instantaneous value at the observation position to which is determined by the second delay portion 709.

Though the titanium sapphire laser is used as the laser portion 709 in the present example, the laser portion 709 is not limited thereto. A small and stable fiber laser may also be used. Suitably, the wavelength of the laser is adjusted to an absorption wavelength of the used carrier generation layer. For example, when indium gallium arsenide (InGaAs) is used as the carrier generation layer, the wavelength of the laser is set to about 1.4 μm. It is sufficient that the carrier generation layer generates carriers by the pump light or the probe light irradiated from the laser portion 708, and hence the material of the carrier generation layer is not limited to those described above.

The first delay portion 704 is constituted of a resin member 713 and an actuator 714. As the resin member 713, polyethylene is used. The resin member 713 has a length of 500 μm in the longitudinal direction of the first electrode 710, a width of 100 μm, and a height of 500 μm. The resin member 713 is located above the element in the vertical direction, with the first electrode 710 being taken as a center. Then, by changing the distance between the resin member 713 and the first electrode 710, the refractive index distribution of the propagation portion is changed to thereby adjust the effective propagation distance (electrical length). Thereby, the time period in which the terahertz wave reaches the second carrier generation layer 718 can be adjusted.

The material and shape of the resin member 713 are not limited to those described above. The material and shape of the resin member 713 are appropriately selected depending on the amount of adjustment, and the material may also be a ceramic material or a semiconductor material. For example, when the amount of adjustment of the effective propagation distance is desired to be increased, a SI—Si substrate having a larger refractive index can also be used. Furthermore, by increasing the size of the resin member 713 in the longitudinal direction to thereby increase the interaction length of the first electrode 710, the amount of adjustment can also be increased.

Here, a piezo element is used as the actuator 714. The resin member 713 and the actuator 714 are bonded to each other. The delay adjustment portion 705 is a control portion and is a driver for driving the piezo element. By expanding and contracting the piezo element, the distance between the resin member 713 and the first electrode 710 is adjusted. An adjustment signal of the delay adjustment portion 705 is output to an arithmetic processing portion, and is utilized for constructing the temporal waveform of the terahertz wave. Incidentally, the arithmetic processing portion is not shown in FIG. 7 but is generally connected to the subsequent stage of the current-voltage conversion portion 723 that constitutes the detection portion, as with the relationship of the correction portion 306 and the arithmetic processing portion 307 to the detection portion 303 in FIG. 3.

Figure 8:
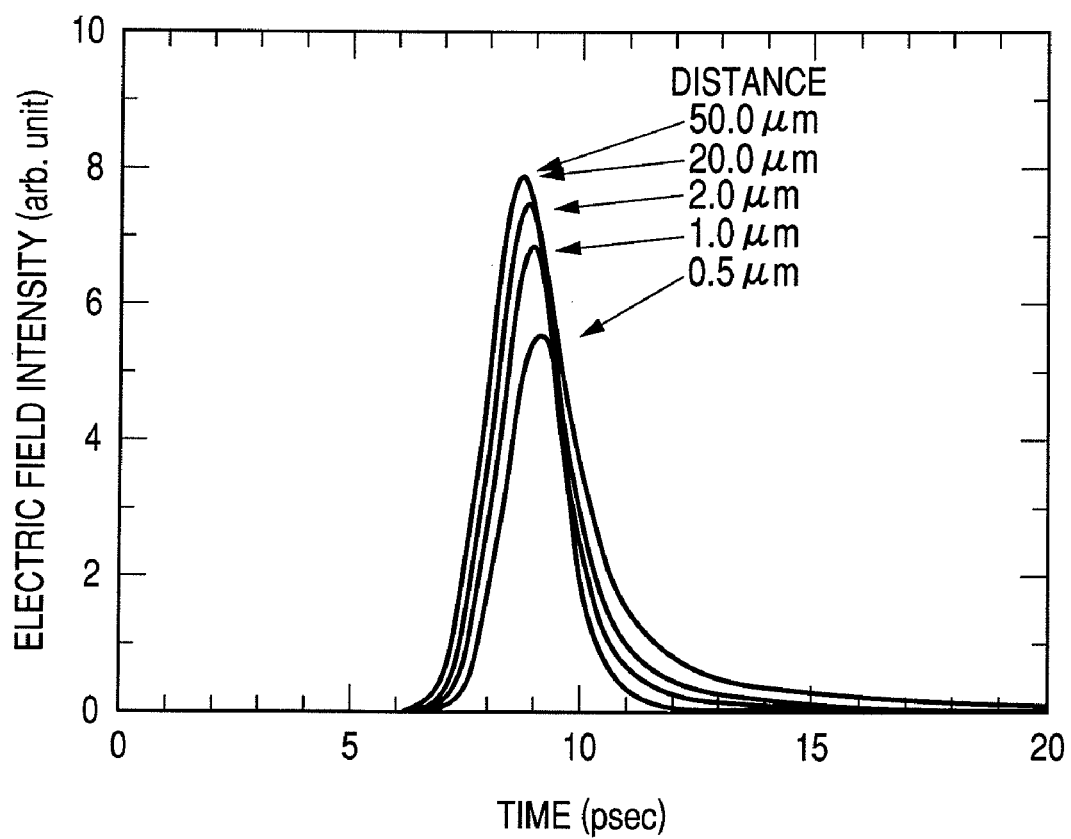
FIG. 8 is a graphical representation showing results of analysis of waveform information of the terahertz wave in Example 1.

FIG. 8 shows the result of analysis of the waveform of the terahertz wave reaching the second carrier generation layer 718 when the resin member 713 is brought close to the first electrode 710, in the present example.

When the distance between the first electrode 710 and the resin member 713 is 20 μm or more, the time at which the terahertz wave reaches the second carrier generation layer 718 does not change. Furthermore, it can be seen that in an area equal to or less than 20 μm, a state where the time at which the terahertz wave reaches the second carrier generation layer is delayed as the distance is decreased. It is shown that the time at which the terahertz wave reaches the second carrier generation layer 718 can be adjusted by about 2 picoseconds with the structure of the present example. The degree of adjustment can be changed by the material or shape of the resin member 713 as described above. In the present example, for example, setting the observation position to in the vicinity of 10 picoseconds by the second delay portion 709, information of the terahertz wave for about 2 picoseconds can be acquired.

Moreover, it can be seen from FIG. 8 that the intensity of the terahertz wave decreases and the pulse width increases as the distance between the first electrode 710 and the resin member 713 is reduced. When the temporal waveform of the terahertz wave is to be constructed, a change in waveform, which is caused with the adjustment, affects the shape of the waveform constructed in the arithmetic processing portion 707. Therefore, in the arithmetic processing portion 707, referring to the correction value in the correction portion 706, a waveform, for which the influence of the transmission line delay device on the waveform of the terahertz wave are restrained, is reconstructed.

A case where the waveform information acquisition apparatus in accordance with the present example is used for inspection of a sample is described with reference to FIG. 7. A sample 720 is disposed on the first electrode 710 not to overlap the resin material 713. The position at which the sample 720 is disposed is between the resin material 713 and the second carrier generation layer 718, specifically, between the transmission line delay device and the detection portion, but the position of the sample 720 is not limited to this mode. For example, the sample 720 may be located between the generation portion and the transmission line delay device.

The terahertz wave detection apparatus in accordance with the present example uses the transmission line delay device as means for sweeping the ultrashort pulse when the temporal waveform of the terahertz wave is to be constructed. Therefore, in comparison with the conventional sweeping means using an optical delay system, the structure can be reduced in size to improve the control speed. In particular, in a device configuration for performing integration processing in order to improve the detection sensitivity for a terahertz wave, since the speed of sweeping the ultrashort pulse is high, a higher detection operation speed can be expected. Moreover, by suppressing the influence of the transmission line delay device on the terahertz wave by using the correction portion, a more practical apparatus can be provided.

Moreover, when the terahertz wave detection apparatus in accordance with the present example is used for inspection of a sample, the inspection can be performed at a higher speed. For example, when the sample involves a change over time (for example, change in water content), an inspection can be performed while suppressing the influence of the change over time.

Next, a method of controlling the first delay portion 704 and the second delay portion 709 when the temporal waveform of the terahertz wave is to be acquired is described with reference to FIGS. 9A, 9B and 9C. A plurality of observation positions t1, t2 and t3 are determined in FIGS. 9A, 9B and 9C by the second delay portion 709. For each of the observation positions t1 to t3, the time period in which the terahertz wave reaches the second carrier generation layer 718 is adjusted by the first delay portion 704.

Figure 9A:
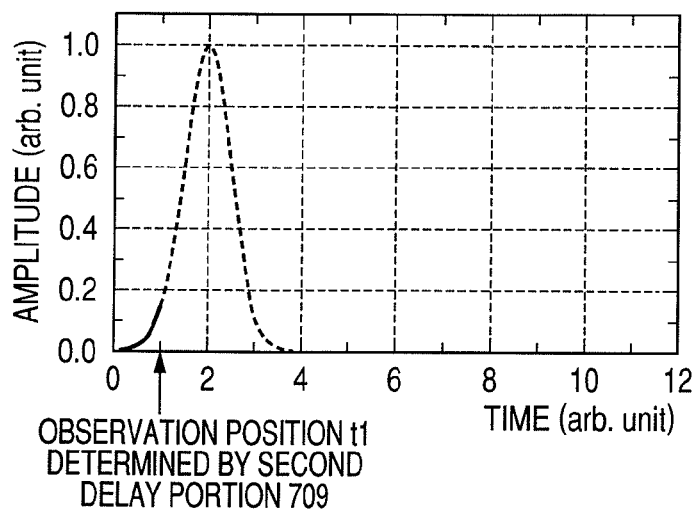
FIGS. 9A, 9B and 9C are graphical representations showing results of analysis of the waveform information of the terahertz wave in Example 1.
Figure 9B:
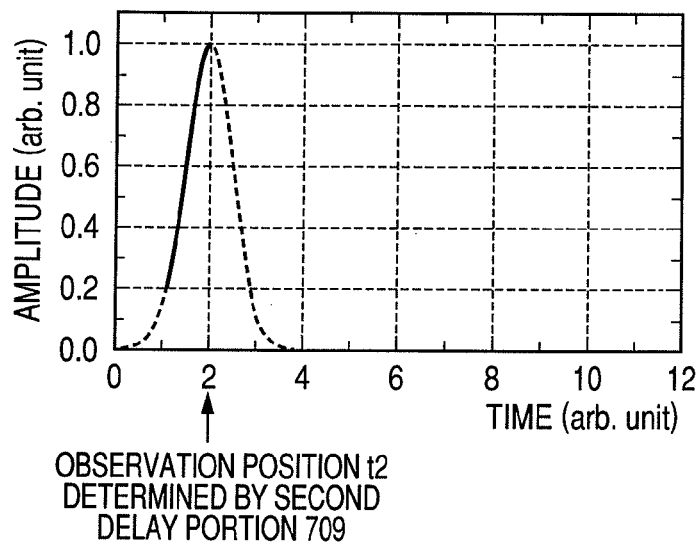
Figure 9C:
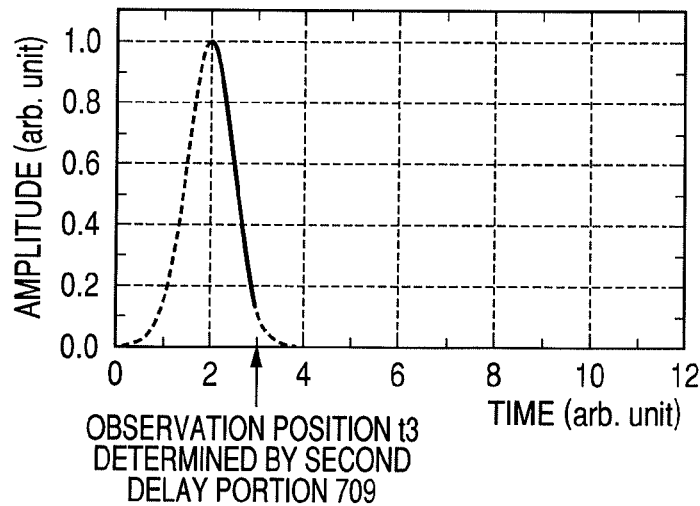

As the temporal waveform of the terahertz wave illustrated in FIGS. 9A, 9B and 9C, a waveform to be input to the transmission line delay device in accordance with the present embodiment is illustrated. The second delay portion 709 sequentially selects the plurality of observation positions t1, t2 and t3. The first delay portion 704 adjusts the time period in which the terahertz wave reaches the second carrier generation layer 718 for each observation position and the temporal waveform of the terahertz wave is constructed in the arithmetic processing portion.

Here, it is assumed that the first delay portion 704 is constituted of the resin material 713 and the actuator 714 and can adjust the time period in which the terahertz wave reaches the second carrier generation layer 718 within the range of 1 picosecond.

The observation position of the second delay portion 709 is adjusted to 1 picosecond (t1 of FIG. 9A). In this state, the first delay portion 704 adjusts the distance from the first electrode 710, and the arithmetic processing portion acquires the temporal waveform of the terahertz wave from 0 picoseconds to the observation position t1. Thereafter, the second delay portion 709 adjusts the observation position to 2 picoseconds (t2 of FIG. 9B). In this state, the first delay portion 704 adjusts the distance from the first electrode 710 again, and the arithmetic processing portion acquires the temporal waveform of the terahertz wave from t1 to t2. Further, for an observation position at 3 picoseconds (t3 of FIG. 9C), the terahertz wave detection apparatus performs the same operation. Such an operation is sequentially performed for a plurality of preset observation positions to acquire the temporal waveform of the terahertz wave. As the temporal waveform of the terahertz wave, which is acquired in the arithmetic processing portion, the temporal waveform corresponding to the amount of adjustment is acquired by the first delay portion 704 from the observation position as a start point (0 seconds) (see waveform (A) of FIG. 5). Therefore, the start point is the same for the temporal waveform at each observation position. Therefore, the arithmetic processing portion refers to the respective observation positions to construct the continuous temporal waveform of the terahertz wave. In the correction portion, the table for correction, which corresponds to the combination of the observation positions, is prepared in advance. In the present example, the arithmetic processing portion selects the table for correction from the correction portion based on the combination of the observation positions, which is used for the construction of the temporal waveform of the terahertz wave, to suppress the influence of the transmission line delay device on the terahertz wave. As described above, the arithmetic processing portion uses the correction values in the table to reconstruct the acquired temporal waveform of the terahertz wave.

With the configuration as described above, the terahertz wave detection apparatus in accordance with the present example and the inspection apparatus using the terahertz wave detection apparatus can acquire the temporal waveform of the terahertz wave for a long period of time even if the amount of adjustment of the transmission line delay device is small.

Example 2

Change in Refractive Index Caused by Using Electrical Means

Figure 10:
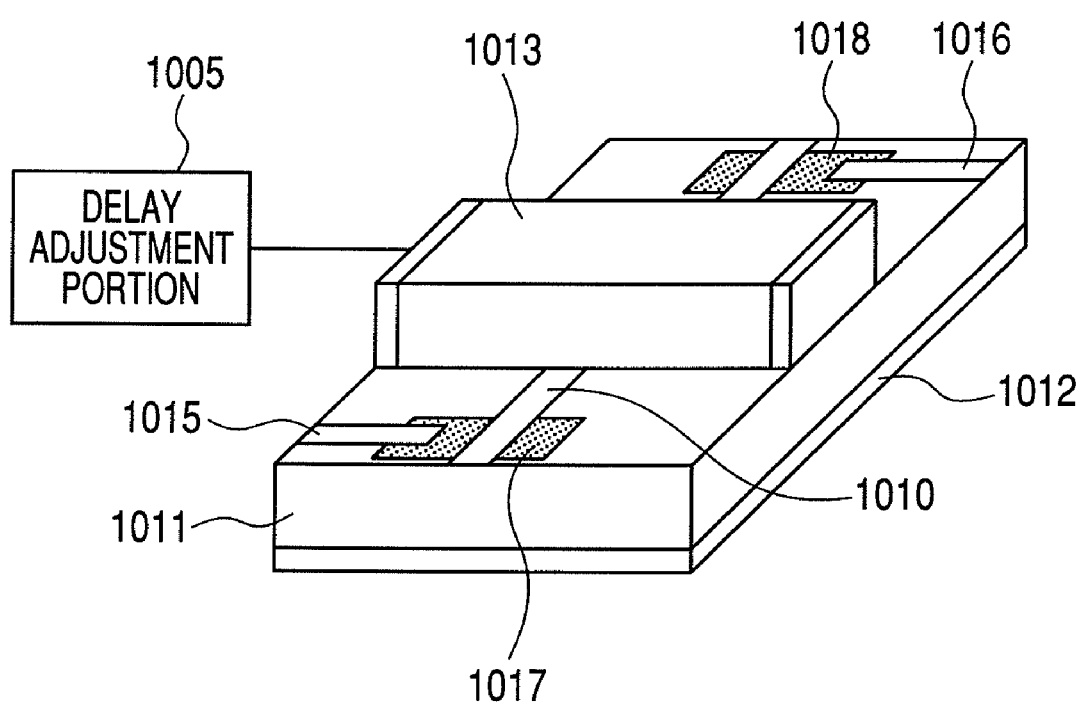
FIG. 10 is a schematic perspective view for illustrating a waveform information acquisition apparatus in accordance with Example 2.

Example 2 is described referring to FIG. 10.

FIG. 10 is a configuration diagram for illustrating the waveform information acquisition apparatus in accordance with the present example. The present example is one mode of the terahertz wave detection apparatus in accordance with the present invention. Specifically, a variation of the above-mentioned transmission line delay device is described.

In Example 1, the refractive index distribution of the propagation portion is mechanically adjusted by using the first delay portion. The present example differs from the other examples in that the refractive index distribution of the propagation portion is electrically adjusted.

In the present example, a liquid crystal member 1013 is used as the first delay portion. As the liquid crystal member 1013, methoxybenzylidene aniline (MBBA) is used. The liquid crystal member 1013 is constituted of MBBA, a cell containing the MBBA, and electrodes for adjusting the orientation of liquid crystal molecules. The liquid crystal member 1013 is provided in contact with a first electrode 1010. A delay adjustment portion 1005 is a control portion for adjusting the orientation of the liquid crystal molecules of the liquid crystal member 1013 through the electrodes constituting the liquid crystal member 1013. By adjusting the orientation of liquid crystal molecules of the liquid crystal member 1013, the refractive index can be adjusted. Other liquid crystal materials can be used as the material of the liquid crystal member 1013. Moreover, the material of the first delay portion is not limited to the liquid crystal material, and may be any material as long as the refractive index can be electrically changed. For example, a mode of adjusting the dispersion of colloids in a colloidal solution can also be employed.

The terahertz wave detection apparatus in accordance with Example 2 and the inspection apparatus using the terahertz wave detection apparatus can electrically adjust the characteristics of the transmission line delay device, and hence further improvement of the control speed can be expected.

In a variation of Example 2, the means for electrically adjusting the refractive index distribution of the propagation portion is not in contact with the first electrode 1010. Furthermore, in another variation of Example 2, there may be employed a configuration in which the distance between the means for electrically adjusting the refractive index distribution of the propagation portion and the first electrode 1010 is made variable.

With such a configuration, the number of adjustable parameters of the characteristics of the transmission line delay device can be increased. As a result, the degree of freedom in the adjustment can be improved in the waveform information acquisition apparatus according to the example and the inspection apparatus using the waveform information acquisition apparatus.

Example 3

Coupling Portion

Example 3 is described with reference to FIGS. 11A and 11B.

Figure 11A:
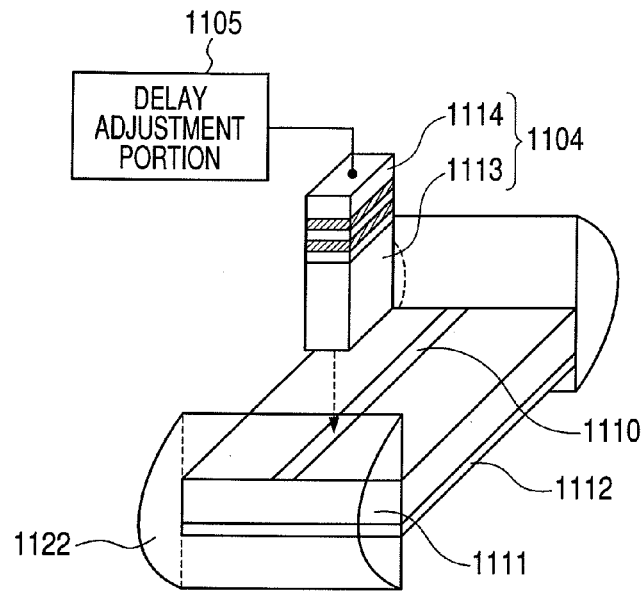
FIGS. 11A and 11B are schematic views for illustrating Example 3.
Figure 11B:
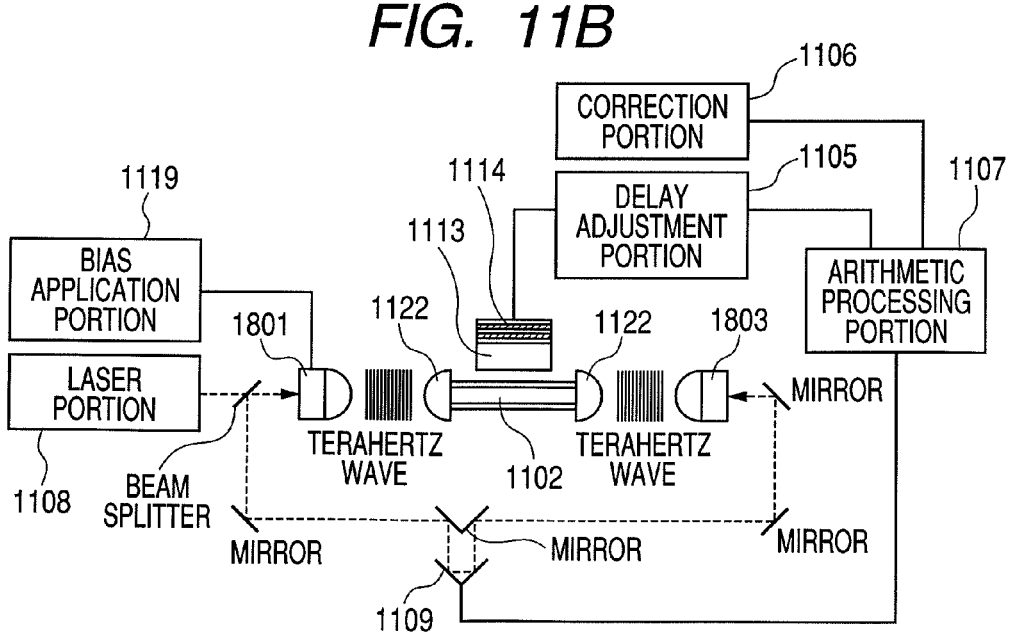

FIGS. 11A and 11B are schematic views for illustrating a waveform information acquisition apparatus including a coupling portion for coupling a terahertz wave to a propagation portion. The present example is one mode related to the terahertz wave detection device in accordance with the present invention. Specifically, a variation of the transmission line delay device described above and an apparatus using the transmission line delay device is described.

Although in the above-mentioned examples the generation portion and the detection portion are integratedly formed in the transmission line delay device, these elements are separated from each other in the present example.

FIG. 11A is a schematic configuration diagram of the transmission line delay device in accordance with the present example. A coupling portion 1122 is connected to a propagation portion 1102. Moreover, a first delay portion 1104 constituted of a resin member 1113 and an actuator 1114 is provided above the propagation portion 1102 in the vertical direction. The refractive index distribution of the propagation portion 1102 can be adjusted by the first delay portion 1104. Although in the present example, the configuration described for Example 1 is used as the first delay portion 1104, the configurations described in the other examples can also be used.

The coupling portion 1122 couples the terahertz wave propagating through the space to the transmission line delay device. The coupling portion 1122 also couples the terahertz wave propagating through the transmission line delay device with the space. A cylindrical lens made of a polyolefin material is used as the coupling portion 1122. However, the material of the coupling portion 1122 is not limited thereto. For example, a semiconductor material such as SI—Si can also be used. Preferably, it is desired to select a material having a small difference between a refractive index of the coupling portion 1122 and that of a dielectric 1111 included in the propagation portion 1102 to avoid unnecessary reflection at the connection boundary between the coupling portion 1122 and the propagation portion 1102.

Here, the shape of the coupling portion 1122 is not limited to the cylindrical lens. A semispherical lens can also be used. A diffraction pattern for coupling to an external electromagnetic field may be inscribed on a first electrode 1110 to form the coupling portion 1122. Further, an antenna may be connected to the propagation portion 1102.

FIG. 11B shows an example of a system configuration diagram when such a transmission line delay device is applied to a terahertz wave detection apparatus. A photoconductive element 1801 is used as a generation portion for generating a terahertz wave by a pump light irradiated from a laser portion 1108. As a detection portion, a photoconductive element 1803 is used. The photoconductive element 1801 is an element having an antenna pattern formed on a semiconductor thin film. As the semiconductor thin film, an SI—GaAs substrate having LT-GaAs grown on a surface thereof is used. Then, a dipole antenna (antenna length: 30 µm; conductor width: 10 µm) made of a conductor obtained by stacking a Ti layer with a thickness of 500 Å and an Au layer with a thickness of 3,000 Å and having a gap of 5 µm at a center thereof is formed on the LT-GaAs. Moreover, as with Example 1 described above, a bias application portion 1119 for applying a bias to the gap is provided. When a terahertz wave is to be generated, for example, the pump light is irradiated to the gap while applying a bias of 10 V to the gap by the bias application portion 1119. As a result, a pulsed terahertz wave having a half width value of about 200 femtoseconds is generated.

The shape of the antenna is not limited to that described above. For example, a bow-tie antenna or a spiral antenna, which is common as a wideband antenna, may also be used. Also, the semiconductor thin film is not limited to that described above, and a semiconductor material such as InGaAs may also be used.

Moreover, the generation portion is not limited to the photoconductive element 1801. For example, a semiconductor material itself may be used as the generation portion. For example, the pump light is irradiated on a mirror-polished surface of GaAs, and by a change over time in instantaneous current generated at this time, a terahertz wave is generated. Further, organic crystal such as 4-dimethylamino-n-methyl-4-stilbazolium Tosylate (DAST) crystal may be used.

The photoconductive element 1803 detects the terahertz wave with a probe light irradiated from the laser portion 1108. As with the photoconductive element 1801, the photoconductive element 1803 is an element including an antenna pattern formed on a semiconductor thin film. Moreover, as with the example described above, the photoconductive element 1803 includes a current-voltage conversion portion (not shown) for detecting the instantaneous current in accordance with the intensity of the electric field of the terahertz wave. The configuration of the detection portion is not limited to the photoconductive element 1803. For example, a heat detector such as a bolometer or a pyroelectric detection element such as Deuterated L-Alanine Triglycine Sulphate (DLATGS) can also be used as the detection portion. Furthermore, there may be used a configuration which uses a DAST crystal as the detection portion and utilizes a Pockels effect as one of the electro-optical effects.

Incidentally, the configuration of the laser portion 1108 is appropriately selected depending on a target of irradiation such as described for Example 1.

In the present example, the configuration allows a terahertz wave to be coupled to the transmission line delay device by using the coupling portion. With such a configuration, the terahertz wave detection apparatus of the present example and the inspection apparatus using the terahertz wave detection apparatus can improve the degree of freedom in device design.

Furthermore, in a variation of the present example, there may be included a mode in which any one of the generation portion and the detection portion is integrated with the transmission line delay device to allow coupling to the outside through a coupling portion.

Figure 12A:
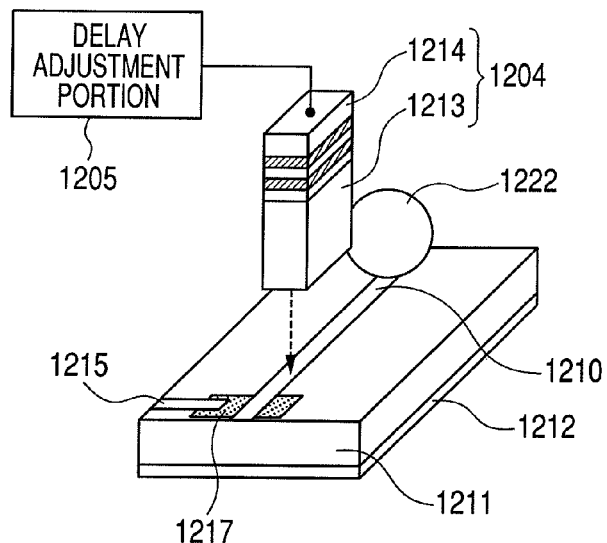
FIGS. 12A and 12B are schematic views for illustrating a variation of Example 3.

FIG. 12A is a schematic configuration diagram of a transmission line delay device in accordance with the variation of Example 3. The generation portion described above is integrated with the propagation portion. Then, a coupling portion 1222 is connected to a first electrode 1210. The coupling portion 1222 has a spherical antenna configuration including a reference electrode 1212 as an earth conductor. The coupling portion 1222 is a silicon sphere having a diameter of 100 μm and coated with Au. The first electrode 1210 and the coupling portion 1222 are fixed by thermocompression bonding. The antenna configuration of the present variation 3 is a wideband antenna having a sensitivity in the vicinity of about 1 THz. Moreover, as described for the example above, the structure of the coupling portion 1222 is not limited thereto.

Figure 12B:
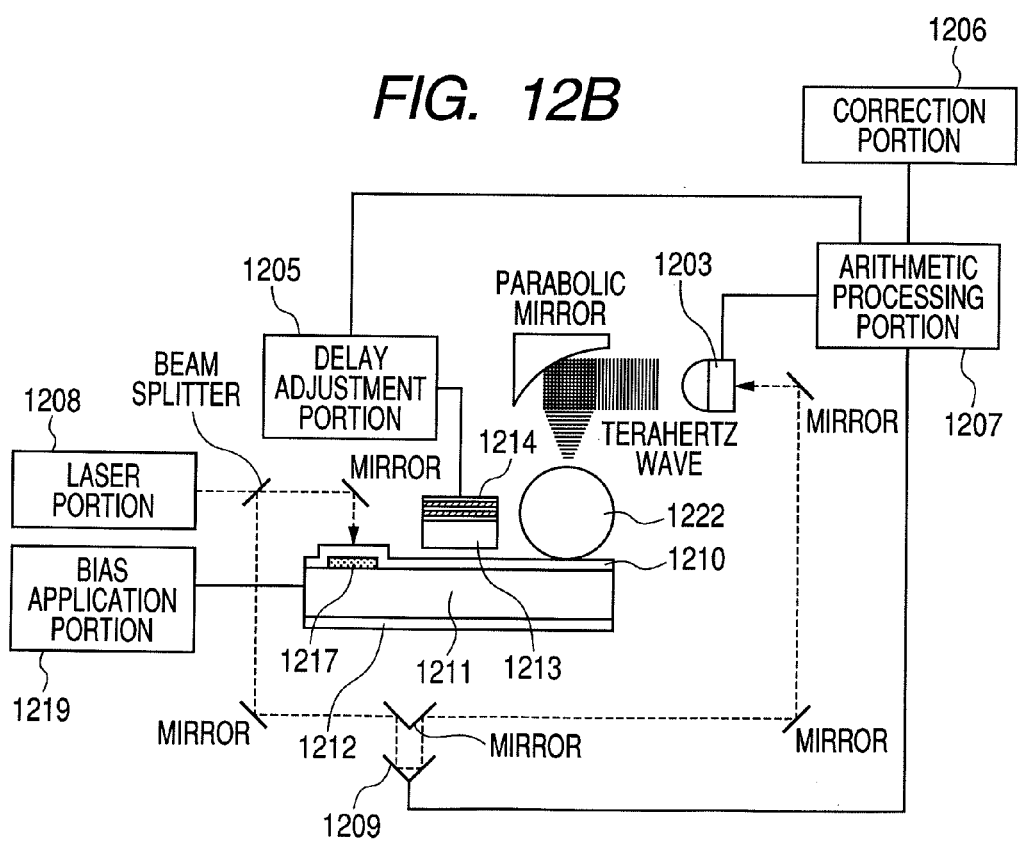

FIG. 12B shows an example of a system configuration diagram when the transmission line delay device is applied to a terahertz wave detection apparatus. A terahertz wave generated from the transmission line delay device integrated with the generation portion is detected by a photoconductive element 1203 provided in the space.

The configuration, in which the generation portion is integrated with the transmission line delay device, is described in the present variation, but a configuration, in which the detection portion is integrated with the transmission line delay device, can also be used. Moreover, the photoconductive element 1203 is used as the detection portion in the present variation, but other modes are also applicable as described for Example 3 above.

The terahertz wave detection apparatus in accordance with the present variation and the inspection apparatus using the terahertz wave detection apparatus have the structure in which the generation portion or the detection portion is integrated with the transmission line delay device, and hence the number of elements to be optically adjusted is reduced to facilitate the handling.

Other Examples

Figure 13:
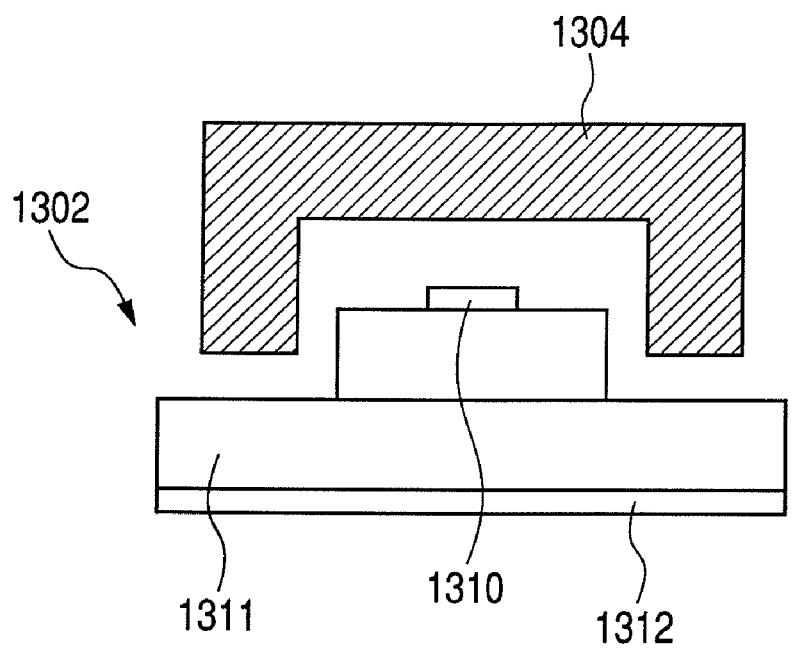
FIG. 13 is a schematic view for illustrating another example.
Figure 14:
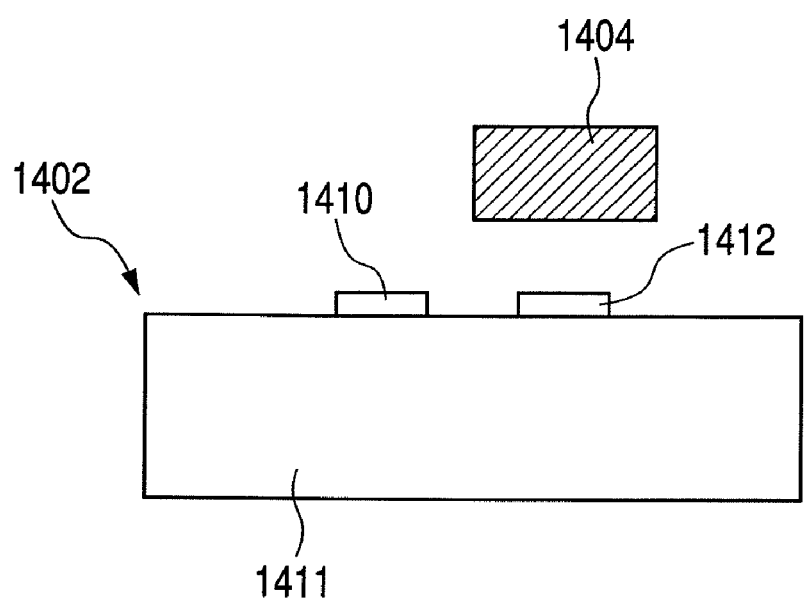
FIG. 14 is a schematic view for illustrating still another example.

The mode of adjusting the refractive index distribution of the propagation portion may have configurations such as illustrated in FIGS. 13 and 14, depending on the structures of the dielectric and the reference electrode.

In a schematic view of FIG. 13, a propagation portion 1302 is a microstrip line type propagation portion. In this mode, a first delay portion 1304 is inserted into a part of a dielectric 1311.

In a schematic view of FIG. 14, a propagation portion 1402 is a strip line type propagation portion. In this mode, the refractive index distribution is adjusted by the arrangement relation between a reference electrode 1412 and a first delay portion 1404.

The positional relation of the first delay portion is not limited as long as the first delay portion can adjust the distribution of the electromagnetic field of the terahertz wave propagating through the propagation portion.

Here, the terahertz wave detection device obtained by appropriately combining the structures and the spirits described in the examples above is provided. Other device structures are not excluded without departing from the sprit of the present invention.

Example 4

Prism

Figure 15A:
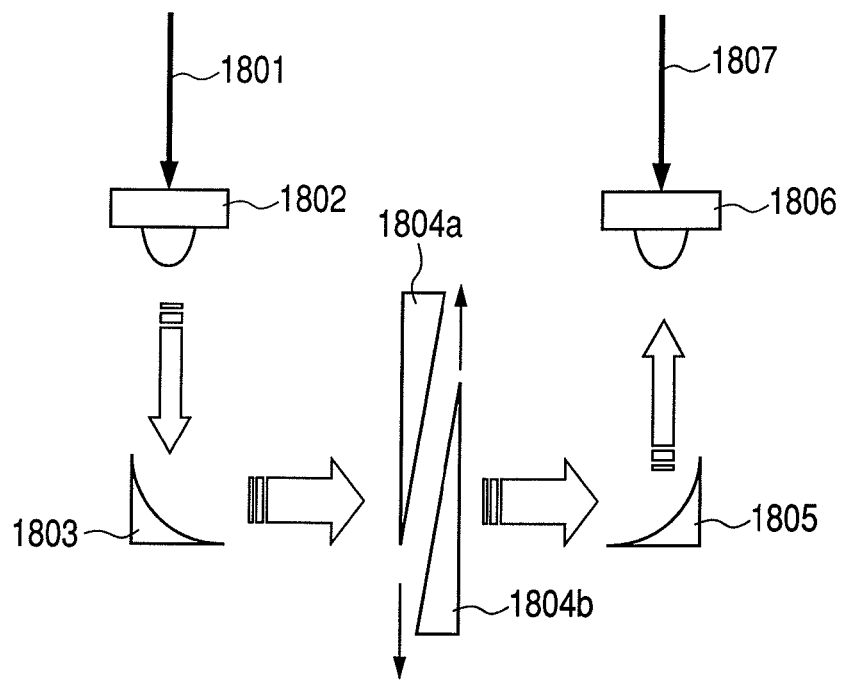
FIGS. 15A, 15B and 15C are schematic views for illustrating a change in optical path length of the terahertz wave in Example 4.

Example 4 is described with reference to FIGS. 15A, 15B and 15C.

A generation-side photoconductive antenna element 1802 for generating a terahertz wave includes a dipole antenna (not shown) formed on LT-GaAs. Pump light 1801 is irradiated to a predetermined position of the dipole antenna of the generation-side photoconductive antenna element 1802 to generate a terahertz wave. The terahertz wave generated from the generation-side photoconductive antenna element 1802 is collimated by a parabolic mirror 1803, reflected by a parabolic mirror 1805, and is incident on a detection-side photoconductive antenna element 1806. Probe light 1807 is incident simultaneously with the incidence of the terahertz wave on the detection-side photoconductive antenna element 1806. As a result, the terahertz wave is detected.

In this case, a pair of dielectric (for example, polyethylene) prisms 1804a, 1804b is inserted into a path of the terahertz wave. Each of the pair of prisms 1804a, 1804b has a surface perpendicular to the optical axis and a surface inclined with respect to the optical axis as illustrated in FIG. 15A. It is preferred that the inclined surfaces of the pair of prisms 1804a, 1804b be parallel to each other. The parallel surfaces are depicted as being apart from each other in FIG. 15A, but the parallel surfaces may be in close contact with each other.

The pair of prisms 1804*a* and 1804*b* serves as a parallel dielectric plate with respect to the terahertz wave. When the pair of prisms 1804*a*, 1804*b* is moved in a direction indicated by an arrow in FIG. 15A, the substantial thickness of the dielectric plates with respect to the terahertz wave is changed (increased).

The increase in the substantial thickness of the pair of prisms 1804*a*, 1804*b* with respect to the terahertz wave increases an optical path length of the terahertz wave. As a result, the timing at which the terahertz wave reaches the detection-side photoconductive antenna element 1806 and the timing at which the probe light 1807 reaches the detection-side photoconductive antenna element 1806 are offset with respect to each other. By using this offset, the temporal waveform of the terahertz wave can be obtained.

Figure 15B:
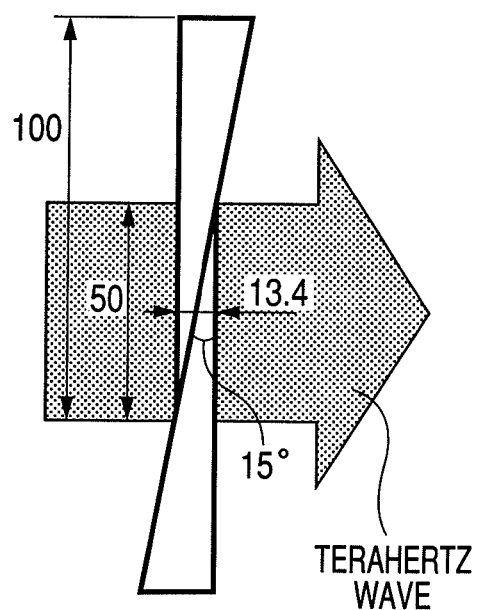
Figure 15C:
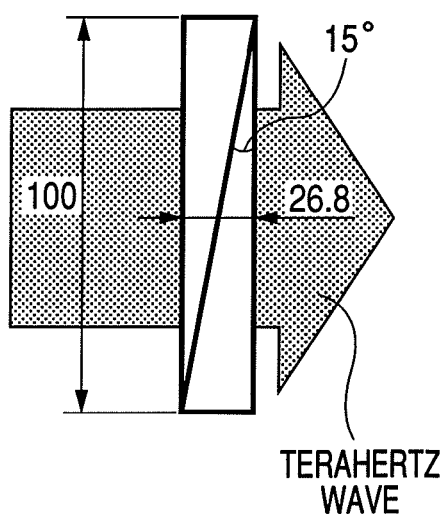

For example, it is assumed that as illustrated in FIGS. 15B and 15C, a pair of polyethylene prisms each having an apex angle of 15° and a length of a surface perpendicular to the terahertz wave traveling direction of 100 mm is used. Furthermore, it is also assumed that the terahertz wave is transmitted through the pair of prisms as a collimated beam having a diameter of 50 mm. When the apex of each of the pair of prisms is present in the vicinity of the center of the other one as illustrated in FIG. 15B, the pair of prisms behaves as a parallel flat polyethylene plate having a thickness of 13.4 mm for the terahertz wave.

When the pair of prisms are completely stacked as illustrated in FIG. 15C, the pair of prisms behaves as a parallel flat polyethylene plate having a thickness of 26.8 mm for the terahertz wave. When it is assumed that the refractive index of polyethylene with respect to the terahertz wave is about 1.5, a change in optical path length of about 20 mm is obtained. This value corresponds to a time delay of about 66 picoseconds in time. Specifically, the temporal waveform of the terahertz wave can be acquired in a time domain of 66 picoseconds.

In the method in accordance with the present example, since the portions related to the generation and detection of the terahertz wave are not moved, there can be obtained such a characteristic of being further resistant against a vibration or the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2007-340392, filed Dec. 28, 2007, and 2008-287755, filed Nov. 10, 2008, which are hereby incorporated by reference herein in their entirety.

The invention claimed is:

1. A waveform information acquisition apparatus for acquiring information regarding a temporal waveform of a terahertz wave, which comprises:
   a generation portion for generating a terahertz wave;
   a detection portion for detecting waveform information of the terahertz wave; and
   a first delay portion for changing a time period from generation of the terahertz wave in the generation portion to detection of the terahertz wave as the waveform information of the terahertz wave in the detection portion,
   wherein the first delay portion is configured so as to change a propagation velocity of the terahertz wave generated by the generation portion, and
   wherein the waveform information of the terahertz wave detected by the detection portion and the propagation velocity are associated with each other for each terahertz wave generated by the generation portion.

2. The waveform information acquisition apparatus according to claim 1, wherein the first delay portion is configured so as to change a refractive index of a region through which the terahertz wave generated by the generation portion propagates.

3. The waveform information acquisition apparatus according to claim 1, wherein the first delay portion is configured to include a member having a refractive index different from a refractive index of a region through which the terahertz wave generated by the generation portion propagates and is also configured so as to change a relative positional relation between the member and the region or a rate at which the member occupies the region.

4. The waveform information acquisition apparatus according to claim 1, further comprising:
   a propagation portion for allowing the terahertz wave generated by the generation portion to propagate therethrough; and
   a control portion for controlling the first delay portion to change the propagation velocity of the terahertz wave propagating through the propagation portion,
   wherein the first delay portion changes the propagation velocity of the terahertz wave generated by the generation portion in the propagation portion.

5. The waveform information acquisition apparatus according to claim 4, wherein the control portion controls a refractive index of a region through which the terahertz wave propagating through the propagation portion propagates to thereby control the propagation velocity of the terahertz wave propagating through the propagation portion.

6. The waveform information acquisition apparatus according to claim 5, wherein the control portion adjusts a distance between the propagation portion and the first delay portion to thereby control the refractive index of the region through which the terahertz wave propagating through the propagation portion propagates.

7. The waveform information acquisition apparatus according to claim 4, wherein the control portion adjusts the first delay portion by use of an electrical means to thereby control a refractive index of a region through which the terahertz wave propagating through the propagation portion propagates.

8. The waveform information acquisition apparatus according to claim 4, further comprising a processing portion for correcting the information regarding the temporal waveform of the terahertz wave detected by the detection portion to provide a shape of the temporal waveform taken before the change of the propagation velocity of the terahertz wave in the propagation portion.

9. The waveform information acquisition apparatus according to claim 8, further comprising:
   a trigger portion for outputting a trigger signal for detecting the terahertz wave by the detection potion; and
   a second delay portion for adjusting a distance between a position at which the trigger signal is output and a position in the detection portion at which the terahertz wave is detected,
   wherein the processing portion uses a correction value prepared from the temporal waveform of the terahertz wave detected by the second delay portion and the first delay portion to correct the temporal waveform of the terahertz wave.

10. The waveform information acquisition apparatus according to claim 9, wherein the trigger signal is light irradiation to the generation portion, and wherein the generation portion or the detection portion is configured to include a carrier generation layer for generating carriers by the light irradiation and generates or detects the terahertz wave by applying an electric field to the carriers.

11. The waveform information acquisition apparatus according to claim 10, further comprising:
- a first electrode for applying the electric field to the carriers; and
- a reference electrode for defining an electric potential serving as a reference of the electric field,
- wherein the propagation portion is configured to include the carrier generation layer, the first electrode, and the reference electrode, and comprises a transmission line through which the terahertz wave generated from the carriers propagates.

12. A waveform information acquisition method comprising:
- allowing a terahertz wave to propagate;
- acquiring waveform information of the terahertz wave propagating at a first propagation velocity;
- changing a propagation velocity of the terahertz wave to a second propagation velocity;
- acquiring waveform information of the terahertz wave propagating at the second propagation velocity; and
- acquiring information regarding a temporal waveform acquired from the waveform information of the terahertz wave propagating at the first propagation velocity and the terahertz wave propagating at the second propagation velocity.

13. The waveform information acquisition method according to claim 12, further comprising correcting the information regarding the temporal waveform to provide a shape of the temporal waveform taken before the change of the propagation velocity of the terahertz wave.

14. A terahertz time domain spectroscopy method comprising:
- generating a terahertz wave;
- allowing the generated terahertz wave to propagate;
- detecting information regarding the propagating terahertz wave; and
- constructing a temporal waveform of the terahertz wave from the detected information regarding the terahertz wave,
- wherein a propagation velocity of the terahertz wave is changed to acquire the temporal waveform.

* * * * *